United States Patent
Croce et al.

(10) Patent No.: US 10,036,018 B2
(45) Date of Patent: Jul. 31, 2018

(54) COMPOSITIONS AND METHODS FOR TREATING CACHEXIA

(71) Applicants: Carlo M. Croce, Columbus, OH (US); Denis C. Guttridge, Upper Arlington, OH (US)

(72) Inventors: Carlo M. Croce, Columbus, OH (US); Denis C. Guttridge, Upper Arlington, OH (US)

( * ) Notice: Subject to any disclaimer, the term of this patent is extended or adjusted under 35 U.S.C. 154(b) by 0 days.

(21) Appl. No.: 15/124,425

(22) PCT Filed: Mar. 10, 2015

(86) PCT No.: PCT/US2015/019667
§ 371 (c)(1),
(2) Date: Sep. 8, 2016

(87) PCT Pub. No.: WO2015/138426
PCT Pub. Date: Sep. 17, 2015

(65) Prior Publication Data
US 2017/0015996 A1   Jan. 19, 2017

Related U.S. Application Data

(60) Provisional application No. 61/950,475, filed on Mar. 10, 2014.

(51) Int. Cl.
| | | |
|---|---|---|
| C07H 21/02 | (2006.01) | |
| C07H 21/04 | (2006.01) | |
| A61K 48/00 | (2006.01) | |
| C12N 15/113 | (2010.01) | |
| A61K 31/7105 | (2006.01) | |
| A61K 45/06 | (2006.01) | |
| A61K 31/713 | (2006.01) | |
| A61K 31/711 | (2006.01) | |

(52) U.S. Cl.
CPC .......... *C12N 15/113* (2013.01); *A61K 31/711* (2013.01); *A61K 31/713* (2013.01); *A61K 31/7105* (2013.01); *A61K 45/06* (2013.01); *C12N 2310/11* (2013.01)

(58) Field of Classification Search
CPC .. C12N 15/113; C12N 2310/11; A61K 31/713
See application file for complete search history.

(56) References Cited

U.S. PATENT DOCUMENTS

| | | |
|---|---|---|
| 2007/0298118 A1 | 12/2007 | Lotvall |
| 2009/0192102 A1 | 7/2009 | Bader et al. |
| 2010/0041734 A1 | 2/2010 | Kandimalla et al. |
| 2012/0070848 A1 | 3/2012 | Rak et al. |
| 2014/0045915 A1 | 2/2014 | Skog et al. |

FOREIGN PATENT DOCUMENTS

| | | |
|---|---|---|
| WO | WO 2002/085396 A1 | 10/2002 |
| WO | WO 2013/034653 A1 | 3/2013 |
| WO | WO 2013/090556 A1 | 6/2013 |
| WO | WO 2015/138426 A1 | 9/2015 |

OTHER PUBLICATIONS

Ali et al. (Gerontology, 2014, 60(4), 294-305).*
Zgheib et al. (Eur Cytokine Netw, 2012, 23(4), 191-197).*
Yamanaka et al. (Blood, 2009, vol. 114, No. 15, pp. 3265-3275).*
Fabbri, M., et al., "MicroRNAs bind to Toll-like receptors to induce prometastatic inflammatory response," *Proceedings of the National Academy of Sciences of the United States of America*, vol. 109, No. 31, pp. E2110-E2116 (2012).
He, W. A., et al., "Microvesicles containing miRNAs promote muscle cell death in cancer cachexia via TLR7," *Proceedings of the National Academy of Sciences of the United States of America*, vol. 111, No. 12, pp. 4525-4529 (2014).
Notification Concerning Transmittal of International Preliminary Report on Patentability for International Application No. PCT/US2015/019667, entitled "Compositions and Methods for Treating Cachexia," dated Sep. 22, 2016.
Notification of Transmittal of the International Search Report and the Written Opinion of the International Searching Authority, or the Declaration for International Application No. PCT/US2015/019667, entitled "Compositions and Methods for Treating Cachexia," dated Jul. 23, 2015.
Soares, R. J., et al. "Involvement of MicroRNAs in the Regulation of Muscle Wasting during Catabolic Conditions," *The Journal of Biological Chemistry*, vol. 289, No. 32, pp. 21909-21925 (2014).

* cited by examiner

*Primary Examiner* — Amy H Bowman
(74) *Attorney, Agent, or Firm* — Hamilton, Brook, Smith & Reynolds, P.C.

(57) ABSTRACT

The present invention relates, in various embodiments, to methods of treating cachexia (e.g., cancer cachexia) in a patient. The methods comprise administering at least one compound for inhibiting, in alternative embodiments, the expression or activity of a microRNA that is present in microvesicles secreted from cancer cells in the patient (e.g., a miR-21 gene product), the expression or activity of a Toll-like receptor (e.g., TLR7, TLR8), the expression or activity of a c-Jun N-terminal kinase (JNK), the secretion of microvesicles from cancer cells, or the fusion of microvesicles from cancer cells with muscle cells or adipocytes. The present invention also relates, in certain embodiments, to pharmaceutical compositions comprising at least two compounds useful in the practice of the methods of the invention described herein.

15 Claims, 14 Drawing Sheets

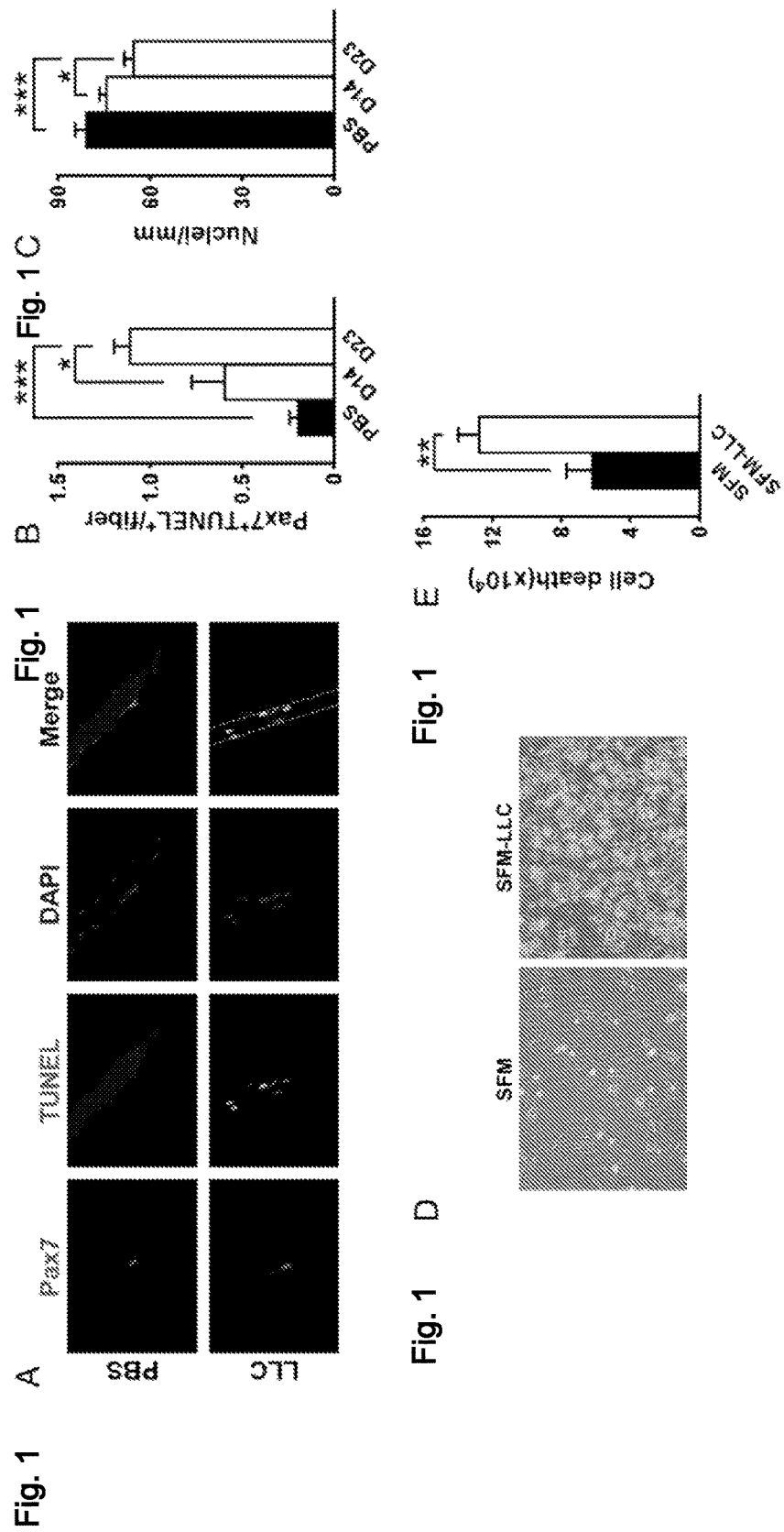

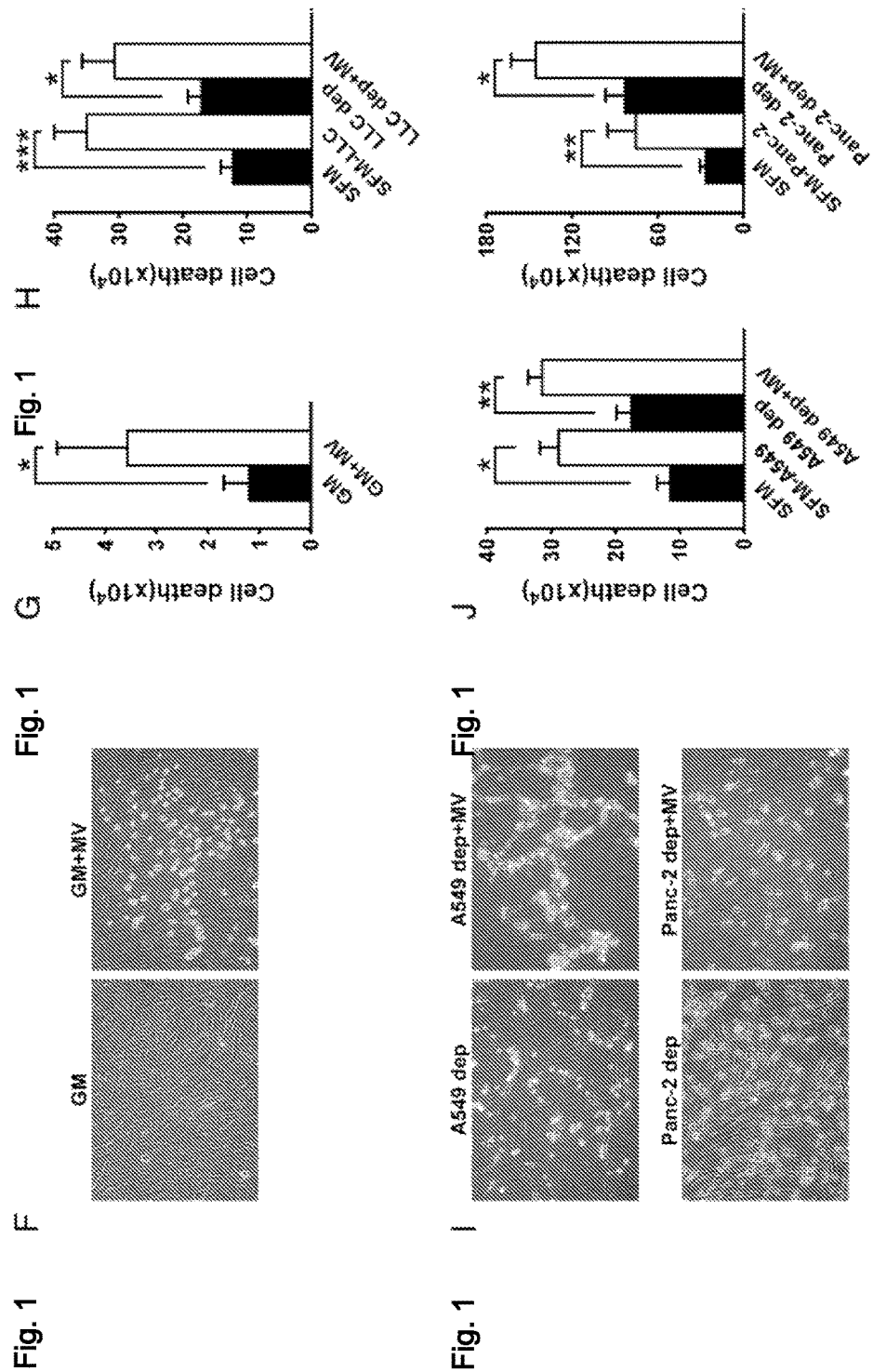

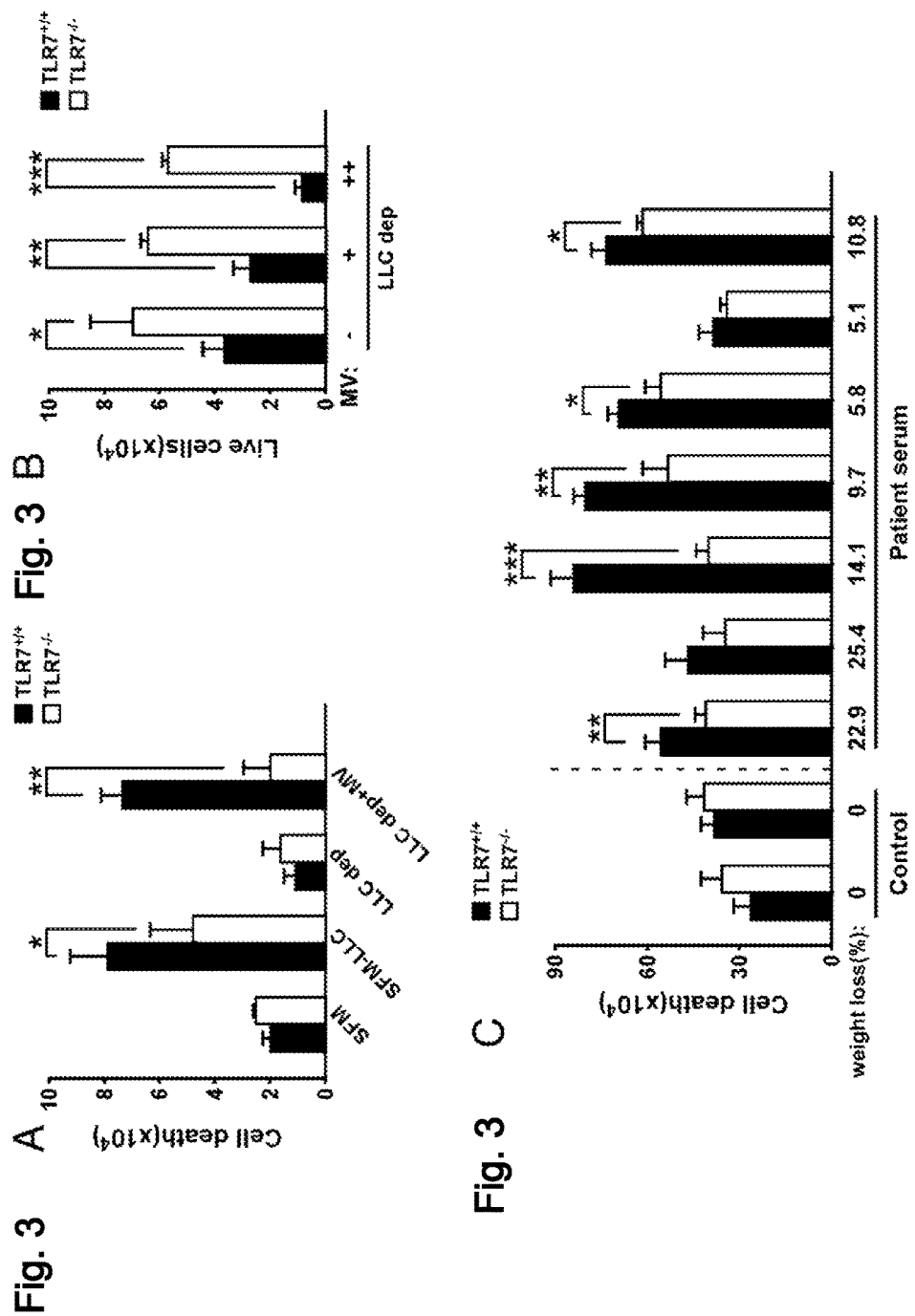

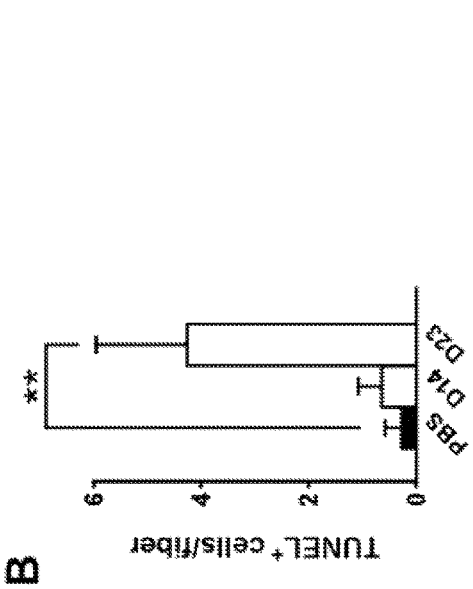
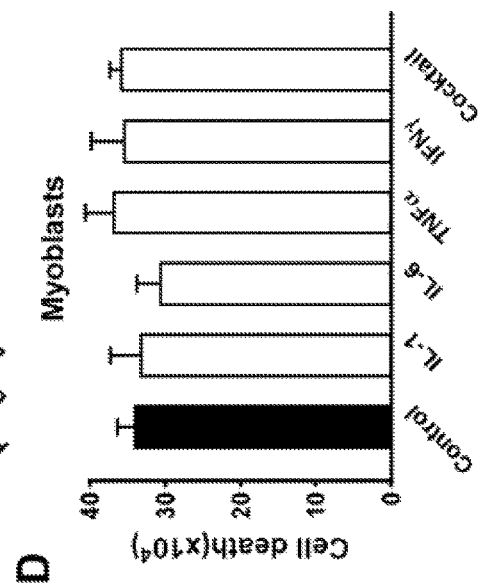
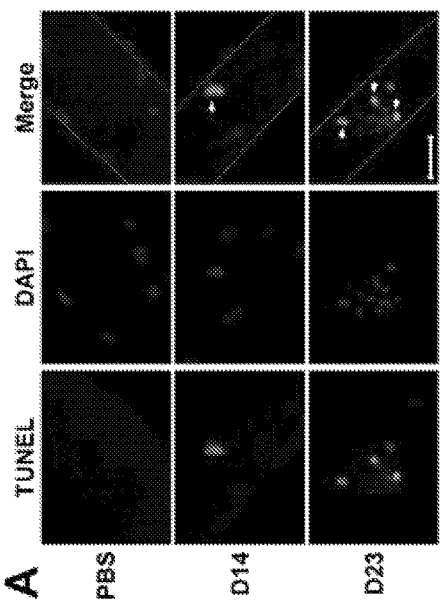
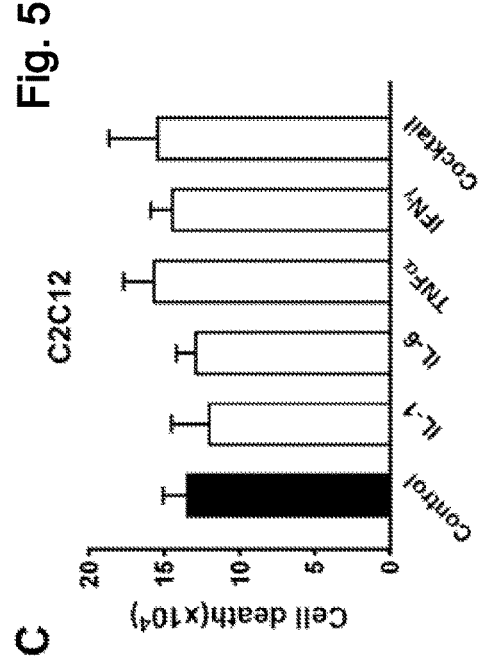
Fig. 5

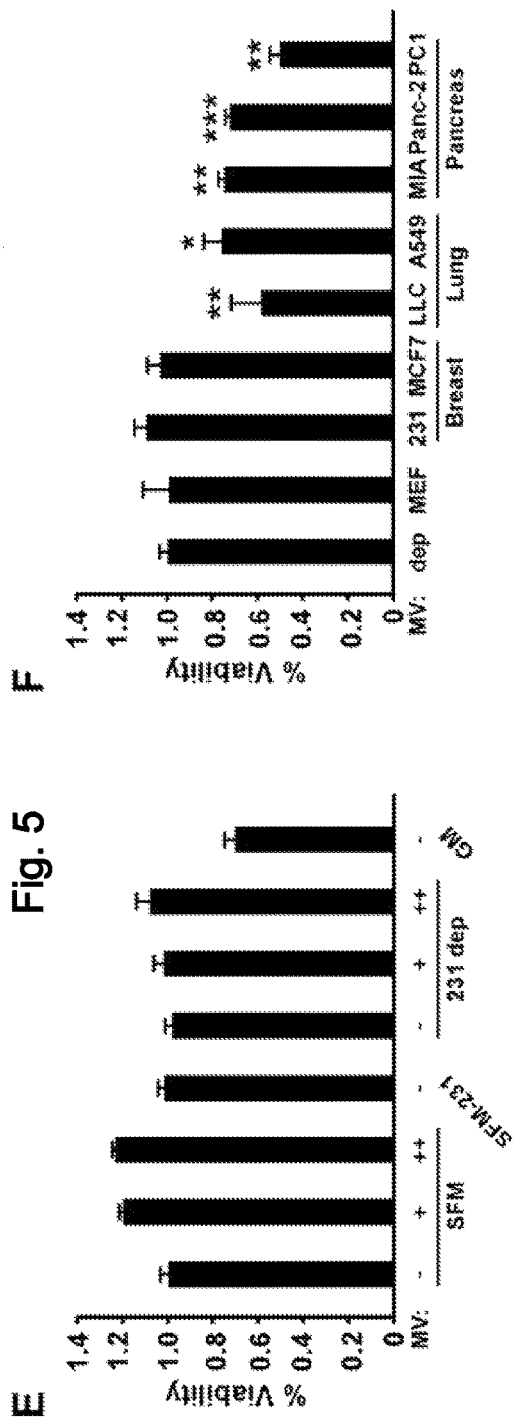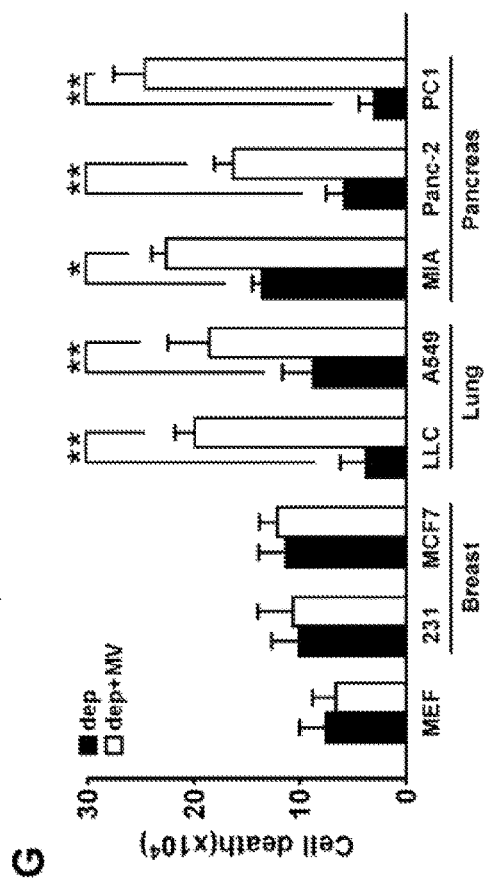
Fig. 5

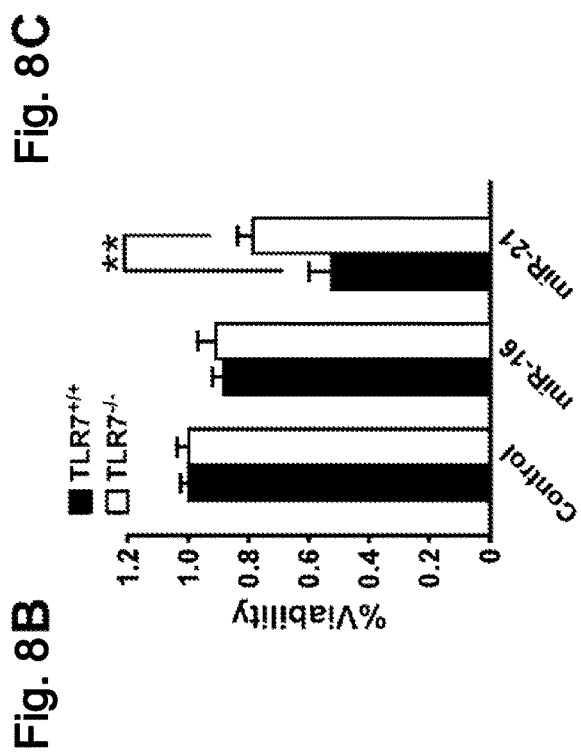
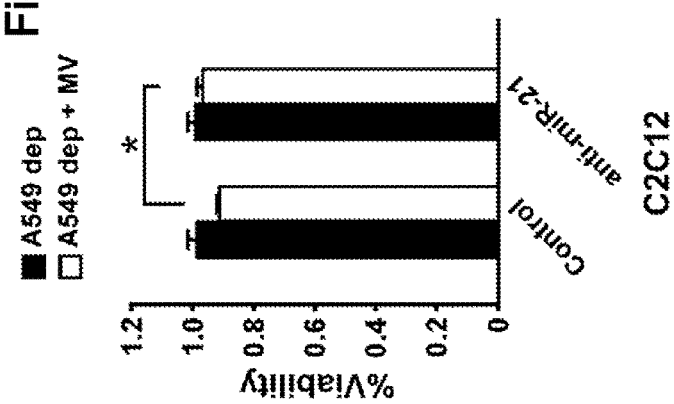
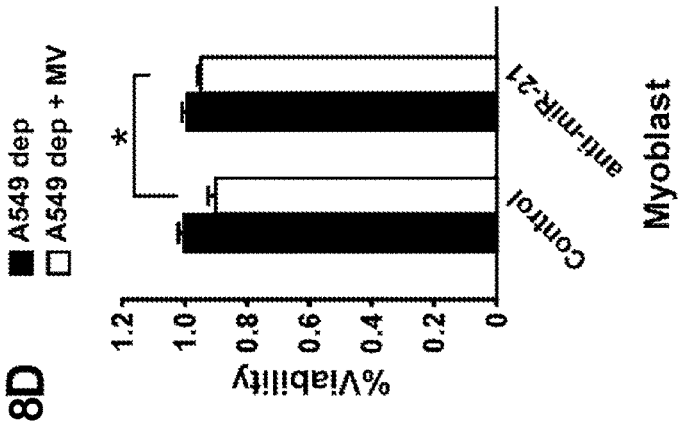
Fig. 8B
Fig. 8C
Fig. 8D

SEQUENCE LISTING

<160> NUMBER OF SEQ ID NOS: 2

<210> SEQ ID NO 1
<211> LENGTH: 72
<212> TYPE: RNA
<213> ORGANISM: Homo sapiens

<400> SEQUENCE: 1
ugucggguag cuuaucagac ugauguugac uguugaaucu cauggcaaca ccagucgaug     60
ggcugucuga ca                                                        72

<210> SEQ ID NO 2
<211> LENGTH: 22
<212> TYPE: RNA
<213> ORGANISM: Homo sapiens

<400> SEQUENCE: 2
uagcuuauca gacugauguu ga                                             22

US 10,036,018 B2

COMPOSITIONS AND METHODS FOR TREATING CACHEXIA

RELATED APPLICATION

This application is the U.S. National Stage of International Application No. PCT/US2015/019667, filed Mar. 10, 2015, which designates the U.S., published in English, and claims the benefit of U.S. Provisional Application No. 61/950,475, filed on Mar. 10, 2014. The entire teachings of the above applications are incorporated herein by reference.

GOVERNMENT SUPPORT

This invention was made with government support under Grant Nos. CA180057 and U01 CA152758 from the National Institutes of Health. The government has certain rights in the invention.

INCORPORATION BY REFERENCE OF MATERIAL IN ASCII TEXT FILE

This application incorporates by reference the Sequence Listing contained in the following ASCII text file:
a) File name: 50501000002SEQLIST; created Sep. 8, 2016, 1 KB in size.

BACKGROUND OF THE INVENTION

Cachexia is a syndrome characterized by weight loss resulting from a reduction of body mass (both lean body and fat mass) that is not caused by malnutrition or starvation. Cachexia occurs with many types of chronic diseases, including cancer, where it is associated with mortality and decreased survival time. About half of all cancer patients develop cachexia, particularly in cases of lung cancer, pancreatic cancer and cancers of the upper gastrointestinal tract. Patients with cachexia suffer from such negative effects as anemia, immunodepression, asthenia, physical weakness, and mental fatigue. In addition, patients with cachexia are more susceptible to dose-limiting chemotoxicity, and the degree of weight loss in cachexia patients is positively correlated with mortality.

In view of the high incidence of cancer in the United States and throughout the world, there is a substantial and immediate need for effective therapeutic agents and methods for treating cachexia in cancer patients.

SUMMARY OF THE INVENTION

The present invention provides, in one embodiment, a method of treating cachexia in a patient in need thereof, comprising administering to the patient (e.g., a human patient with cancer) an effective amount of at least one compound for inhibiting the expression or activity of a miR-21 gene product (e.g., an antisense nucleic acid that binds to a miR-21 gene product).

In another embodiment, the invention relates to a method of treating cancer cachexia in a patient in need thereof, comprising administering to the patient an effective amount of at least one compound for inhibiting the expression or activity of a microRNA that is contained in microvesicles secreted from cancer cells in the patient (e.g., miR-21, miR-27b, miR-29a, miR-92a, miR-126, miR-133, miR-146, miR-147, miR-155, miR-574-5p, or a combination thereof).

In yet another embodiment, the present invention relates to a method of treating cachexia in a patient in need thereof, comprising administering to the patient an effective amount of at least one compound for inhibiting the expression or activity of a Toll-like receptor 7 (TLR7 receptor) or a Toll-like receptor 8 (TLR8 receptor).

In a further embodiment, the present invention relates to a method of treating cachexia in a patient in need thereof, comprising administering to the patient an effective amount of at least one compound for inhibiting the expression or activity of a c-Jun N-terminal kinase (JNK).

In an additional embodiment, the present invention relates to a method of treating cachexia in a patient who has a cancer, comprising administering to the patient an effective amount of at least one compound for inhibiting secretion of microvesicles (e.g., microvesicles containing a miR-21 gene product) from cancer cells in the patient.

In yet another embodiment, the present invention relates to a method of treating cachexia in a patient who has a cancer, comprising administering to the patient an effective amount of at least one compound for inhibiting fusion of microvesicles (e.g., microvesicles containing a miR-21 gene product) from cancer cells with muscle cells or adipocytes in the patient.

In a further embodiment, the present invention relates to a pharmaceutical composition comprising at least two compounds selected from the group consisting of a compound for inhibiting the expression or activity of a microRNA that is present in microvesicles secreted from cancer cells, compound for inhibiting the expression or activity of a Toll-like receptor 7 (TLR7 receptor) or a Toll-like receptor 8 (TLR8 receptor), a compound for inhibiting the expression or activity of a c-Jun N-terminal kinase (JNK), a compound for inhibiting secretion of microvesicles from cancer cells, and a compound for inhibiting fusion of microvesicles from cancer cells with muscle cells or adipocytes.

In its various embodiments, the present invention provides several therapeutic targets, compositions and methods for treating cachexia and its effects in patients suffering from cancer and other diseases.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A shows immunofluorescent images of single myofibers isolated from in vivo xenograft LLC mouse models. As control, myofibers derived from PBS-injected mice were used. Pax7 is shown in red, TUNEL is shown in green, nuclei staining (DAPI) is shown in blue, and their colocalization is shown in the Merge panels. Staining was performed 14 and 23 days (D14 and D23, respectively) after tumor injection.

FIG. 1B is a graph depicting TUNEL quantitation related to immunofluorescence shown in FIG. 1A.

FIG. 1C is a graph depicting the number of nuclei per single myofiber.

FIG. 1D shows images of C2C12 cells incubated with LLC-conditioned medium (SFM-LLC) for 4 h. Serum-free medium (SFM) was used as a negative control.

FIG. 1E is a graph depicting cell death as determined with Trypan blue dye staining. Serum-free medium (SFM) was used as a negative control.

FIG. 1F shows images of C2C12 cells incubated with LLC-derived MVs (GM+MV). Growth medium (SFM) was used as negative control.

FIG. 1G is a graph depicting cell death as assessed with Trypan blue dye staining.

FIG. 1H is a graph depicting cell death as assessed with Trypan blue staining on C2C12 cells incubated with MV-depleted medium (LLC dep) and LLC-derived MVs (LLC dep+MV).

FIG. 1I shows images showing C2C12 cell death induced by A549- and Panc-2-derived MVs.

FIG. 1J are graphs depicting C2C12 cell death induced by A549-derived MVs (left graph) or Panc-2-derived MVs (right graph). Data are combined from at least three independent experiments. Results are presented as average±SD. $*P \leq 0.05$; $P \leq 0.01$; $*P \leq 0.001$.

FIG. 2A is a graph depicting results of a Trypan blue assay performed on C2C12 cells incubated for 24 h with MVs isolated from xenograft B6 mouse model-derived serum (LLC serum). As control, MVs isolated from normal mouse serum were used. Results are presented as average±SEM. $*P \leq 0.05$; $P \leq 0.01$; $*P \leq 0.001$.

FIG. 2B is a graph depicting results of a Trypan blue assay performed on primary myoblasts incubated for 20 h with MVs isolated from cachectic patient sera (Patient serum). As control, MVs isolated from normal patient sera were used. Results are presented as average±SEM. $*P \leq 0.05$; $P \leq 0.01$; $*P \leq 0.001$.

FIG. 3A is a graph depicting results of Trypan blue dye staining performed on primary myoblasts isolated from TLR7+/+ and TLR7−/− B6 mice and incubated with LLC-derived MVs (LLC dep+MV) for 48 h. As controls, myoblasts incubated with serum-free medium (SFM), LLC-conditioned medium (SFM-LLC), and LLC MV-depleted medium (LLC dep) were used. Results are presented as average±SEM. $*P \leq 0.05$; $P \leq 0.01$; $*P \leq 0.001$.

FIG. 3B is a graph depicting live cell number as determined using a cell counter after 5 d of incubation with MVs. MVs were resuspended in MV-depleted medium. "+" or "++" indicate a low or high amount of MVs being used to treat myoblasts. Results are presented as average±SEM. $*P \leq 0.05$; $P \leq 0.01$; $*P \leq 0.001$.

FIG. 3C is a graph depicting myoblast cell death assessed by trypan blue dye staining twenty hours after primary myoblasts isolated from TLR7+/+ and TLR7−/− B6 mice were incubated with MVs isolated from control serum of healthy donors (n=2) or cachectic serum (n=7) of pancreatic cancer patients with cachexia. Results are presented as average±SEM. $*P \leq 0.05$; $P \leq 0.01$; $*P \leq 0.001$.

FIG. 5A are images showing TUNEL staining performed on single myofibers isolated from in vivo xenograft LLC mouse models 14 and 23 d after tumor injection (D14 and D23, respectively). As negative control, myofibers derived from PBS-injected mice (PBS) were used. (Scale bar, 20 μm.)

FIG. 5B is a graph depicting quantitation of TUNEL+ cells in FIG. 5A.

FIG. 5C is a graph depicting cell death assessed by trypan blue dye staining performed on C2C12 cells that were treated for 24 h with individual cytokines or a mixture (Cocktail) of IL-1, IL-6, TNFα, and IFNγ (all at 5 ng/mL). As a negative control, cells were treated with serum-free medium.

FIG. 5D is a graph depicting cell death assessed by trypan blue dye staining performed on primary myoblasts that were treated for 24 h with individual cytokines or a mixture (Cocktail) of IL-1, IL-6, TNFα, and IFNγ (all at 5 ng/mL). As a negative control, cells were treated with serum-free medium.

FIG. 5E is a graph depicting results of an MTS assay performed on primary myoblasts incubated for 8 h with breast cancer cell line MDA-MB-231-derived MVs, diluted either in serum-free medium (SFM) or in SFM depleted of MVs (231 dep). As control, SFM from MDA-MB-231 cells (SFM-231) and growth medium (GM) were used. "+" or "++" indicate a low or high amount of MVs being used to treat myoblasts.

FIG. 5F is a graph depicting results of an MTS assay performed on C2C12 cells incubated with MVs isolated from the indicated cell lines. As control, C2C12 cells were also incubated with SFM depleted of MVs or MEF-derived MVs. Results are presented as average±SEM. $*P \leq 0.05$; $P \leq 0.01$; $*P \leq 0.001$.

FIG. 5G is a graph depicting results of a Trypan blue assay performed on C2C12 cells with different tumor-derived MVs and their corresponding MV-depleted media. Treatment with MEF-derived MVs was used as control. Treatments with MVs derived from MDA-MB-231, MIA-PaCa-2, and AsPC-1 are indicated as 231, MIA, and PC1, respectively. Results are presented as average±SEM. $*P \leq 0.05$; $P \leq 0.01$; $*P \leq 0.001$.

DETAILED DESCRIPTION OF THE INVENTION

Figure 4B:
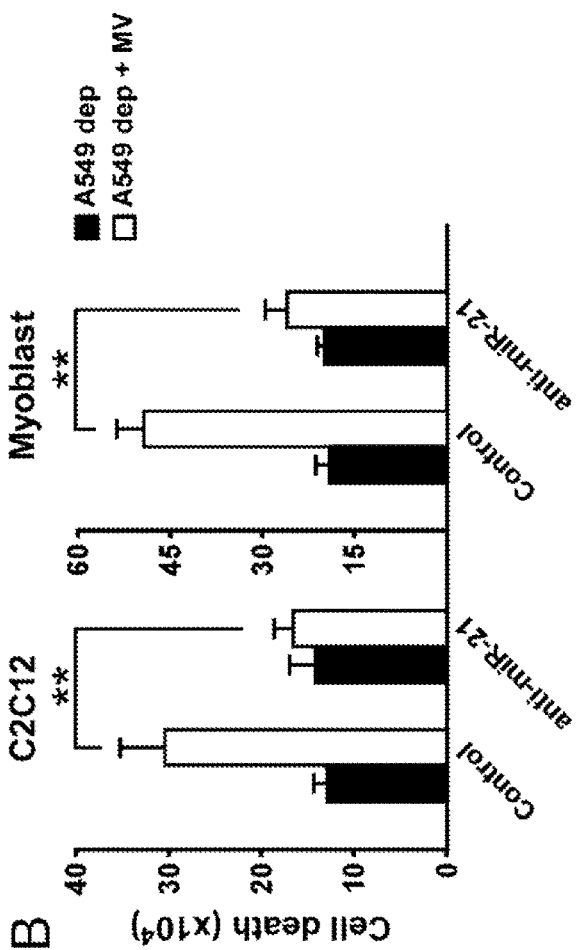
FIG. 4B is a graph depicting a determination of live primary myoblasts after incubation for 24 h with MVs isolated from A549 cells previously transfected with LNA-antinegative control and LNA-anti-miR-21. Experiments were performed in quadruplicate. Results are presented as average±SEM. $*P \leq 0.05$; $P \leq 0.01$; $*P \leq 0.001$.

The present invention is based, in part, on the inventors' finding that cancer cells (e.g., tumor cells) secrete microRNAs (e.g., miR-21) in microvesicles (MVs)/exosomes, which circulate in the cancer patient and can fuse with the plasma membrane of skeletal muscle cells in the patient. Once delivered to the skeletal muscle cells, the microRNAs bind to Toll-like receptors on the skeletal muscle cells and initiate a signaling cascade involving c-Jun N-terminal kinase (JNK) and leading to apoptosis.

Without wishing to be bound by any one theory, it is believed that cachexia can be prevented and/or treated (e.g., inhibited, reduced, ameliorated) in a patient (e.g., a patient who has cancer) by inhibiting the expression and/or activity of certain tumor-derived microRNAs (e.g., miR-21) that are capable of inducing apoptosis of skeletal muscle cells (e.g., myoblasts) and cells in adipose tissue (e.g., adipocytes).

Accordingly, in one embodiment, the invention relates to a method of treating cachexia (e.g., cancer cachexia) in a patient who is in need of treatment, comprising administering to the patient an effective amount of a compound for inhibiting the expression or activity of a miR-21 gene product.

"Cachexia," also known as "wasting sydrome," is a condition characterized by loss of body mass, mainly in skeletal muscle and adipose tissue, that cannot be reversed nutritionally. Cachexia is frequently observed in patients with cancer, AIDS, chronic obstructive lung disease, multiple sclerosis, congestive heart failure, tuberculosis, familial amyloid polyneuropathy, mercury poisoning (acrodynia) and hormonal deficiency. Cachexia that is associated with cancer is also known as "cancer cachexia." A skilled medical professional (e.g., physician) can readily detect cachexia in a patient.

As used herein, the terms "treat," "treating," and "treatment" mean to counteract (e.g., reduce the probability/likelihood of developing, delay the onset of, lessen the severity of) one or more symptoms of cachexia to the extent that the cachexia is improved according to a clinically-acceptable standard.

As used herein, "patient" refers to a mammal (e.g., human, dog, cat, horse, cow). Preferably, the patient is a human (e.g., a human who has, or is at risk for developing, cachexia). A "patient in need thereof" refers to a patient who has, or is at risk for developing, cachexia. A skilled medical professional (e.g., physician) can readily determine whether a patient has, or is at risk for developing, cachexia.

In certain embodiments, the patient has a condition associated with cachexia. "Conditions associated with cachexia" typically precede, and are an underlying cause of, the cachexia. Such conditions include, for example, cancer, AIDS, chronic obstructive lung disease, multiple sclerosis, congestive heart failure, tuberculosis, familial amyloid polyneuropathy, mercury poisoning (acrodynia), and hormonal deficiency.

In a particular embodiment, the patient has cancer. Cachexia is relatively common in patients with certain types of cancer (e.g., lung cancer and cancers of the upper gastrointestinal (GI) tract), but is less common in patients having other types of cancer (e.g., breast cancer and cancers of the lower GI tract). Accordingly, in one embodiment, the patient has lung cancer. In another embodiment, the patient has a cancer of the upper GI tract (e.g., esophageal cancer, stomach/gastric cancer, duodenal cancer). In yet another embodiment, the patient has pancreatic cancer.

In the practice of the present method, an effective amount of at least one compound for inhibiting the expression and/or activity of a miR-21 gene product (also referred to herein as a "miR-21 inhibitor compound") is administered to a patient (e.g., a human patient with cachexia).

As used herein, a "miR-21 gene product" refers to both the unprocessed, or precursor, miR-21 RNA product of a miR-21 gene and the processed, or mature, miR-21 RNA product of a miR-21 gene. In one embodiment, the miR-21 gene product is the unprocessed precursor miR-21 RNA product of the human wild type miR-21 gene which has the nucleotide sequence:

(SEQ ID NO: 1)
UGUCGGGUAGCUUAUCAGACUGAUGUU
GACUGUUGAAUCUCAUGGCAACACCAGUCGAUGGGCUGUCUGACA.

In another embodiment, the miR-21 gene product is the processed mature miR-21 RNA product of the human wild type miR-21 gene, which has the nucleotide sequence UAGCUUAUCAGACUGAUGUUGA (SEQ ID NO:2).

As used herein, "inhibiting the expression of a miR-21 gene product" means inhibiting (e.g., decreasing, reducing, eliminating) the production or formation of a miR-21 gene product in a cell (e.g., by inhibiting transcription of a gene encoding a miR-21 gene product, by inhibiting the processing of a precursor miR-21 gene product).

"Inhibiting the activity of a miR-21 gene product" refers to inhibiting (e.g., decreasing, reducing, eliminating) one or more activities of a mature miR-21 gene product. Such activities include, but are not limited to, binding of miR-21 gene product to a miR-21 target molecule (e.g., a nucleic acid target, a miR-21 receptor protein (e.g., a TLR7 receptor, a TLR8 receptor)) or cell signaling (e.g., cell signaling that leads to apoptosis).

As used herein, an "effective amount" is an amount sufficient to achieve a desired therapeutic or prophylactic effect under the conditions of administration, such as an amount sufficient to inhibit (i.e., reduce, decrease, prevent) the loss of skeletal muscle and/or adipose tissue in a patient who has, or is at risk for developing, cachexia. The effectiveness of a therapy (e.g., the reduction and/or elimination of loss of skeletal muscle and/or adipose tissue) can be determined by a skilled medical professional.

A skilled medical professional can also determine an effective amount of miR-21 inhibitor compound for a given patient, e.g., by taking into account factors such as the size and weight of the subject; the extent of disease penetration; the age, health and sex of the subject; the route of administration; and whether the administration is regional or systemic. For example, an effective amount of a miR-21 inhibitor compound can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be at least about 10 micrograms/gram of tumor mass, and is preferably between about 10-500 micrograms/gram of tumor mass. More preferably, the effective amount is at least about 60 micrograms/gram of tumor mass. In one embodiment, an effective amount of a miR-21 inhibitor compound is at least about 100 micrograms/gram of tumor mass.

An effective amount of a miR-21 inhibitor compound can also be based on the approximate or estimated body weight of a subject to be treated. Preferably, such effective amounts are administered parenterally or enterally, as described herein. For example, an effective amount of a miR-21 inhibitor compound administered to a subject can range from about 5-3000 micrograms/kg of body weight, and is preferably between about 700-1000 micrograms/kg of body weight, and is more preferably greater than about 1000 micrograms/kg of body weight.

One skilled in the art can also readily determine an appropriate dosage regimen for the administration of a miR-21 inhibitor compound to a given subject. For example, a miR-21 inhibitor compound can be administered to the subject once (e.g., as a single injection or deposition). Alternatively, a miR-21 inhibitor compound can be administered once or twice daily to a subject for a period of from about three to about twenty-eight days, more preferably from about seven to about ten days. In a preferred dosage regimen, a miR-21 inhibitor compound is administered once a day for seven days. Where a dosage regimen comprises multiple administrations, it is understood that an effective amount of the miR-21 inhibitor compound can be the total amount of the compound that is administered to the patient over the entire dosage regimen.

Exemplary miR-21 inhibitor compounds that are suitable for use in the methods described herein include, but are not limited to, antisense nucleic acids, double-stranded RNA (such as short- or small-interfering RNA or "siRNA") and enzymatic RNA molecules such as ribozymes. Each of these compounds can be targeted to a given miR-21 gene product and inhibit the expression and/or one or more activities of the miR-21 gene product, e.g., by destroying or inducing the destruction of the target miR-21 gene product, or by inhibiting the binding of the miR-21 gene product to a complementary target mRNA.

In a particular embodiment, the miR-21 inhibitor compound is an antisense nucleic acid. As used herein, an "antisense nucleic acid" refers to a nucleic acid molecule that binds (e.g., hybridizes) to a target nucleic acid (e.g., a miR-21 gene product) by means of, for example, RNA-RNA, RNA-DNA, RNA-LNA or RNA-peptide nucleic acid interactions (e.g., Watson-Crick base pairing interactions). Antisense nucleic acids that bind to microRNA targets include anti-miRNA oligonucleotides (AMOs) and antagomirs.

Antisense nucleic acids suitable for use in the present methods are typically single-stranded nucleic acids (e.g., RNA, DNA, LNA, RNA-DNA chimeras, PNA) that comprise a nucleic acid sequence that is complementary to a contiguous nucleic acid sequence in a miR-21 gene product. Preferably, the antisense nucleic acid comprises a nucleic acid sequence that is at least about 50%, 60%, 70%, 80% or 90% complementary to a contiguous nucleic acid sequence in a miR-21 gene product. Preferably the antisense nucleic acid comprises a nucleic acid sequence that is at least about 95% complementary, more preferably at least about 99% complementary, to a contiguous nucleic acid sequence in a miR-21 gene product. In a particular embodiment, the antisense nucleic acid comprises a nucleic acid sequence that is 100% complementary to a contiguous nucleic acid sequence in a miR-21 gene product.

In some embodiments, antisense nucleic acids can contain one or more chemical modifications (e.g., cholesterol moieties, duplex intercalators such as acridine, or nuclease-resistant groups) to the nucleic acid backbone, the sugar, the base moieties (or their equivalent), or a combination thereof. Such modifications can, in various embodiments, enhance target specificity, nuclease resistance, delivery and/or other properties related to the therapeutic efficacy of the molecule. Preferred chemical modifications include, 2'-O-methyl (2'-O-Me), 2'-O-methoxyethyl (2'-MOE) and 2'-fluoro (2'-F) modifications, among others, at the 2' position of the sugar moieties. In a particular embodiment, the antisense nucleic acid is a locked nucleic acid (LNA).

Exemplary antisense nucleic acids that can bind to, and inhibit, miR-21 expression and/or activity are available commercially and include, for example, miRVana™ and Ambion® Anti-mir™ inhibitors of miR-21 (Life Technologies), anti-miR-21 oligonucleotides (Integrated DNA Technologies, San Diego, Calif.), miScript miR-21 inhibitor (Qiagen) and MISSION® Lenti miR-21 inhibitor (Sigma-Aldrich, St. Louis, Mo.).

miR-21 inhibitor compounds can also be isolated double-stranded RNA ("dsRNA") molecules that induce RNA interference of miR-21 expression. Such dsRNAs preferably have at least 90%, for example about 95%, 98%, 99% or 100%, sequence homology with at least a portion of a miR-21 gene product. In preferred embodiments, the dsRNA molecules are "short hairpin" (shRNA) or "small interfering" RNA (siRNA).

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target miR gene product.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in one embodiment, the siRNA comprises at least one 3' overhang of from 1 to about 6 nucleotides (which includes ribonucleotides or deoxyribonucleotides) in length, preferably from 1 to about 5 nucleotides in length, more preferably from 1 to about 4 nucleotides in length, and particularly preferably from about 2 to about 4 nucleotides in length. In a preferred embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. published patent application 2002/0173478 to Gewirtz and in U.S. published patent application 2004/0018176 to Reich et al., the entire disclosures of which are herein incorporated by reference.

miR-21 inhibitor compounds can also be enzymatic nucleic acids. As used herein, an "enzymatic nucleic acid" refers to a nucleic acid comprising a substrate binding region that has complementarity to a contiguous nucleic acid sequence of a miR gene product, and which is able to specifically cleave the miR gene product. Preferably, the enzymatic nucleic acid substrate binding region is 50-100% complementary, more preferably 75-100% complementary, and most preferably 95-100% complementary to a contiguous nucleic acid sequence in an miR gene product. The enzymatic nucleic acids can also comprise modifications at the base, sugar, and/or phosphate groups. An exemplary enzymatic nucleic acid for use in the present methods is a ribozyme.

Production of miR-21 Inhibitor Compounds

A miR-21 inhibitor compound can be produced synthetically (e.g., by chemical synthesis) or, in some embodiments, recombinantly (e.g., by expression from a recombinant plasmid or viral vector) using methods known in the art. Exemplary methods for producing and testing a miR-21 inhibitor compound, including antisense nucleic acids, siRNAs and ribozymes, are well known in the art; see, e.g., Stein and Cheng (1993), Science 261:1004 and U.S. Pat. No. 5,849,902 to Woolf et al., Werner and Uhlenbeck (1995), Nucl. Acids Res. 23:2092-96; Hammann et al. (1999), Antisense and Nucleic Acid Drug Dev. 9:25-31; and U.S. Pat. No. 4,987,071 to Cech et al, the entire disclosures of which are herein incorporated by reference.

In some embodiments, a miR-21 inhibitor compound can be chemically synthesized, e.g., using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, a miR-21 inhibitor compound can be expressed from recombinant circular or linear DNA plasmids containing a suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible, or regulatable, promoters for expression of a miR-21 inhibitor compound in cells.

A miR-21 inhibitor compound expressed from a recombinant plasmid can be isolated from cultured cell expression systems by standard techniques. Preferably, a recombinant plasmid expressing the miR-21 inhibitor compound is delivered to and expressed in the cells of a patient undergoing treatment, as discussed herein below.

A person skilled in the art can select a suitable plasmid (e.g., DNA plasmid) for expressing a miR-21 inhibitor compound, methods for inserting nucleic acid sequences into the plasmid to express the gene products, and methods of delivering the plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296: 550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

Preferably, a miR-21 inhibitor compound is expressed from a single plasmid. In one embodiment, a plasmid expressing a miR-21 inhibitor compound comprises a sequence encoding the compound under the control of the CMV intermediate-early promoter. As used herein, "under the control" of a promoter means that the promoter initiates and directs transcription of the nucleic acid sequence(s) encoding the miR-21 inhibitor compound.

A miR-21 inhibitor compound can also be expressed from one or more recombinant viral vectors. A miR-21 inhibitor compound expressed from a recombinant viral vector can be isolated (e.g., from cultured cell expression system) by standard techniques, or can be expressed directly in cells of a patient. The use of recombinant viral vectors to deliver the miR gene products to a patient's cells is discussed in more detail below.

Recombinant viral vectors can include sequences encoding the miR-21 inhibitor compound and a suitable promoter for expressing the compound. Suitable promoters include, for example, the U6 or H1 RNA pol III promoter sequences, or the cytomegalovirus promoters. Selection of other suitable promoters is within the skill in the art. The recombinant viral vectors can also comprise inducible or regulatable promoters for expression of the compound in a cell.

Exemplary viral vectors for expressing a miR-21 inhibitor compound include, without limitation, vectors derived from adenovirus (AV); adeno-associated virus (AAV); retroviruses (e.g., lentiviruses (LV), Rhabdoviruses, murine leukemia virus); herpes virus, and the like. Preferred viral vectors include vectors derived from AV and AAV. A suitable AV vector and method for expressing a miR-21 inhibitor compound in target cells are described in Xia et al. (2002), *Nat. Biotech.* 20:1006-1010, the entire disclosure of which is herein incorporated by reference. A suitable AAV vector for expressing a miR-21 inhibitor compound in target cells are described in Samulski et al. (1987), *J. Virol.* 61:3096-3101; Fisher et al. (1996), *J. Virol.*, 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference. Preferably, a miR-21 inhibitor compound is expressed from a single recombinant AAV vector comprising the CMV intermediate early promoter.

In one embodiment, a miR-21 inhibitor compound is expressed from a recombinant AAV viral vector that includes a nucleic acid sequence encoding the miR-21 inhibitor compound in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the sequences from the vector, the polyT termination signals act to terminate transcription.

The tropism of the viral vectors can be modified by pseudotyping the vectors with envelope proteins or other surface antigens from other viruses, or by substituting different viral capsid proteins, as appropriate. For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J. E. et al. (2002), *J Virol* 76:791-801, the entire disclosure of which is herein incorporated by reference.

Methods for the selection, modification, delivery and expression of recombinant viral vectors suitable for use in the present invention are known in the art (see, e.g., Dornburg (1995), *Gene Therap.* 2:301-310; Eglitis (1988), *Biotechniques* 6:608-614; Miller (1990), *Hum. Gene Therap.* 1:5-14; and Anderson (1998), *Nature* 392:25-30, the entire disclosures of which are herein incorporated by reference). Dosage, Administration and Delivery of miR-21 Inhibitor Compounds Suitable means for delivering inhibitor compounds to a subject can readily be determined by persons of skill in this art. For example, inhibiting compounds can be administered by methods suitable to transfect cells of the subject with these compounds, or with nucleic acids comprising sequences encoding these compounds. Preferably, the cells are transfected with a plasmid or viral vector comprising sequences encoding at least one miR gene product or miR gene expression inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

An inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Preferred administration routes are injection, infusion and direct injection into the tumor.

In the present methods, an inhibiting compound can be administered to the subject either as naked RNA, in combination with a delivery reagent, or as a nucleic acid (e.g., a recombinant plasmid or viral vector) comprising sequences that express the miR gene product or expression inhibiting compound. Suitable delivery reagents include, e.g, the Mirus Transit TKO lipophilic reagent; lipofectin; lipofectamine (e.g., Lipofectamine® 2000 (Life Technologies)); cellfectin; polycations (e.g., polylysine), and liposomes.

Recombinant plasmids and viral vectors comprising sequences that express the miR gene products or miR gene expression inhibiting compounds, and techniques for delivering such plasmids and vectors to cancer cells, are discussed above.

In a preferred embodiment, liposomes are used to deliver an inhibiting compound (or nucleic acids comprising sequences encoding them) to a subject. Liposomes can also increase the blood half-life of the gene products or nucleic acids.

Liposomes suitable for use in the invention can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369, the entire disclosures of which are herein incorporated by reference.

The liposomes for use in the present methods can comprise a ligand molecule that targets the liposome to target cells (e.g., skeletal muscle cells, such as myoblasts; adipose tissue cells, such as adipocytes). Ligands which bind to receptors prevalent in skeletal muscle cells, such as monoclonal antibodies that bind to antigens expressed on the surface of skeletal muscle cells, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH$_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), Proc. Natl. Acad. Sci., USA, 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression inhibition compounds (or nucleic acids comprising sequences encoding them) to tumor cells.

Pharmaceutical Formulations

A miR-21 inhibitor compound is preferably formulated as a pharmaceutical composition, sometimes called a "medicament" or "formulation," according to techniques known in the art, prior to administering the compound to a patient. As used herein, a "pharmaceutical composition" includes formulations for human and veterinary use. Typically, pharmaceutical compositions are characterized as being sterile and pyrogen-free. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

A pharmaceutical composition useful for the methods described herein typically includes at least one miR-21 inhibitor compound (or at least one nucleic acid encoding a miR-21 inhibitor compound), or a physiologically acceptable salt thereof, mixed with a pharmaceutically-acceptable carrier. In some embodiments, the miR-21 inhibitor compounds are encapsulated by liposomes (e.g., liposomes targeting smooth muscle cells, liposomes targeting adipocytes) in the pharmaceutical composition.

The pharmaceutical compositions of the invention that include at least one miR-21 inhibitor compound can, in certain embodiments, include one or more additional therapeutic agents. Such compositions are useful as combination therapies. Additional therapeutic agents that are suitable for the present inventions include, but are not limited to, one or more agents useful for treating cachexia and one or more agents useful for treating a disorder associated with cachexia (e.g., cancer).

Therapeutic agents that are useful for treating cachexia in a patient include, for example, the inhibitor compounds described herein as being useful for treating cachexia, such as compounds for inhibiting the expression or activity of a Toll-like receptor 7 (TLR7 receptor) or a Toll-like receptor 8 (TLR8 receptor), compounds for inhibiting the expression or activity of a c-Jun N-terminal kinase (JNK), compounds for inhibiting secretion of microvesicles from cancer cells, and compounds for inhibiting fusion of microvesicles from cancer cells with muscle cells or adipocytes. Additional agents for treating cachexia in a patient include appetite stimulants, supplemental nutrients, omega-3 fatty acids, 5-HT$_3$ antagonists and Cox-2 inhibitors.

Therapeutic agents that are useful for treating cancer and which are suitable for inclusion in the pharmaceutical formulations of the invention include, for example, chemotherapy agents (e.g., tamoxifen, cisplatin, mitomycin, 5-fluorouracil, doxorubicin, sorafenib, octreotide, dacarbazine (DTIC), Cis-platinum, cimetidine, cyclophophamide) and hormone therapy agents (e.g., anti-estrogen compounds, luteinizing hormone-releasing hormone (LH-RH) agonists, aromatase inhibitors (e.g., anastrozole, exemestane, letrozole), and estrogen receptor modulators (e.g., tamoxifen, raloxifene, toremifene)).

Additional therapeutic agents that can be included in the pharmaceutical compositions of the invention include agents for mitigating the effects of cachexia or underlying disease (e.g., cancer), or the side effects of the therapeutic agents for treating such conditions, such as agents for managing pain (e.g., narcotics), antacids, anti-vertigo medications, anti-nausea medications, and the like, all of which are readily appreciated by the person skilled in the art.

In a particular embodiment, the present invention relates to a pharmaceutical composition comprising at least two compounds selected from the group consisting of a compound for inhibiting the expression or activity of a microRNA that is present in microvesicles secreted from cancer cells (e.g., miR-21), compound for inhibiting the expression or activity of a Toll-like receptor 7 (TLR7 receptor) or a Toll-like receptor 8 (TLR8 receptor), a compound for inhibiting the expression or activity of a c-Jun N-terminal kinase (JNK), a compound for inhibiting secretion of microvesicles from cancer cells, and a compound for inhibiting fusion of microvesicles from cancer cells with muscle cells or adipocytes.

Suitable pharmaceutically-acceptable carriers for inclusion in the pharmaceutical compositions of the invention are well known in the art. Preferred pharmaceutically-acceptable carriers include, e.g., water, buffered water, normal saline, 0.4% saline, 0.3% glycine, and hyaluronic acid.

In a preferred embodiment, the pharmaceutical compositions of the invention comprise at least one miR-21 inhibitor compound (or at least one nucleic acid comprising sequences encoding such a compound) which is resistant to degradation by nucleases. One skilled in the art can readily synthesize nucleic acids which are nuclease resistant, for example by incorporating one or more ribonucleotides that are modified at the 2'-position into the miR gene products. Suitable 2'-modified ribonucleotides include those modified at the 2'-position with fluoro, amino, alkyl, alkoxy, and O-allyl.

Suitable pharmaceutical compositions for the methods described herein can also comprise conventional pharmaceutical excipients and/or additives. Such pharmaceutical excipients include, but are not limited to, stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate).

The pharmaceutical compositions can be packaged for use in liquid form or, alternatively, can be in solid form (e.g., a tablet, a pill, a lyophilized powder). For solid pharmaceutical compositions, conventional nontoxic solid pharmaceutically-acceptable carriers can be used (e.g., pharmaceutical grades of mannitol, lactose, starch, magnesium stearate, sodium saccharin, talcum, cellulose, glucose, sucrose, magnesium carbonate).

A solid pharmaceutical composition for oral administration typically includes about 10-95% by weight, preferably about 25%-75% by weight, of a miR-21 inhibitor compound or nucleic acid encoding the miR-21 inhibitor compound.

A pharmaceutical composition for aerosol (inhalational) administration typically includes about 0.01-20% by weight, preferably about 1%-10% by weight, of a miR-21 inhibitor compound or nucleic acid encoding the miR-21 inhibitor compound encapsulated in a liposome as described above, and a propellant. A carrier can also be included as desired; e.g., lecithin for intranasal delivery.

Additional Methods of the Invention

Without wishing to be bound by any particular theory, it is believed that cancer cells secrete different microRNAs in exosomes (e.g., microvesicles), particularly in cancers that have been associated with the overexpression of one or more microRNAs, and that at least some of these microRNA can promote cachexia when the microvesicles that carry them fuse with skeletal muscle cells and/or adipoctyes in the patient. Thus, in another embodiment, the invention relates to a method of treating cancer cachexia in a patient in need thereof, comprising administering to the patient an effective amount of at least one compound for inhibiting the expression or activity of a microRNA that is contained in microvesicles secreted from cancer cells in the patient (e.g., miR-21).

As used herein, "microvesicles," collectively refers to exosomes, circulating microvesicles, shedding microvesicles, ectosomes, microparticles, epididimosomes, argosomes, exosome-like vesicles, promininosomes, prostasomes, dexosomes, texosomes, dex, tex, archeosomes and oncosomes. Generally, microvesicles are extracellular organelles which are released, or shed, into the microenvironment and are composed of fragments of plasma membrane typically ranging from 50 nm to 1000 nm.

Suitable compounds for inhibiting the expression or activity of a microRNA that is contained in (e.g., encapsulated by, embedded in) microvesicles secreted from cancer cells include compounds for inhibiting the expression and/or activity of microRNAs that have been detected as being overexpressed in particular cancers, also known as oncomirs. Preferably, the compound for inhibiting the expression or activity of a microRNA that is contained in microvesicles secreted from cancer cells inhibits the expression and/or activity of a microRNA selected from the group consisting of miR-21, miR-27b, miR-29a, miR-92a, miR-126, miR-133, miR-146, miR-147, miR-155 and miR-574-5p, or a combination thereof (e.g., miR-21 and miR-29a). The nucleotide sequences of the precursor and mature forms of these and other human microRNAs are well known and can readily be obtained, e.g., from miRBase: searchable database of published miRNA sequences and annotation.

Compounds for inhibiting the expression or activity of microRNAs that are contained in microvesicles secreted from cancer cells can be formulated, dosed, administered and delivered as described above for miR-21 inhibitor compounds.

The present invention is also based, in part, on the inventors' finding that miR-21 molecules secreted from cancer cells promote apoptosis by activating Toll-like receptors (TLRs) on myoblasts. Accordingly, in a further embodiment, the present invention relates to a method of treating cachexia in a patient in need thereof, comprising administering to the patient an effective amount of at least one compound for inhibiting the expression or activity of a Toll-like receptor (TLR) (e.g., TLR7 receptor, TLR8 receptor).

Preferably, the compound for inhibiting the expression or activity of a TLR can inhibit the interaction between miR-21 and TLR7 and/or TLR8.

Exemplary compounds for inhibiting the expression or activity of a TLR include, for example, include the TLR7 and TLR8 inhibitors IMO-3100 and IMO-8400 (Idera Pharmaceuticals, Cambridge, Mass.) undergoing clinical studies for therapeutic use and the TLR inhibitors described in U.S. Pat. Nos. 8,357,665 and 8,377,898 to to Kandimalla, et al., the relevant contents of which are incorporated herein by reference.

Compounds for inhibiting the expression or activity of a TLR that are suitable for use in the methods described herein can be formulated, dosed, administered and delivered as described above for miR-21 inhibitor compounds.

The present invention is further based, in part, on the inventors' finding that miR-21 molecules secreted from cancer cells promote apoptosis of myoblasts through c-Jun N-terminal kinase (JNK) activity. Thus, in another embodiment, the invention relates to a method of treating cachexia in a patient in need thereof, comprising administering to the patient an effective amount of at least one compound for inhibiting the expression or activity of a c-Jun N-terminal kinase (JNK).

JNK inhibitors for therapeutic use are known in the art and include those described in Graczyk, P. P., *Future Medicinal Chemistry* 5(5): 539-551 (2013) and Bubici, C. and Papa, S., *British Journal of Pharmacology* 171: 24-37 (2014), the relevant contents of which are incorporated herein by reference.

Compounds for inhibiting the expression or activity of a JNK that are suitable for use in the methods described herein can be formulated, dosed, administered and delivered as described above for miR-21 inhibitor compounds.

The present invention is additionally based, in part, on the inventors' finding that miR-21 molecules in microvesicles secreted from cancer cells promote apoptosis of cells at sites located distally from the tumor. Therefore, in yet another embodiment, the present invention relates to a method of treating cachexia in a patient who has a cancer, comprising administering to the patient an effective amount of at least one compound for inhibiting secretion of microvesicles (e.g., microvesicles containing one or more microRNAs that are overexpressed in the cancer cells) from cancer cells in the patient. In a particular embodiment, the microvesicles contain a miR-21 gene product.

Inhibitors of microvesicle secretion include the compound GW4869 discussed in Fabbri, M., *PNAS* 109(31): E2110-2116 (2012), the relevant contents of which are incorporated herein by reference.

Compounds for inhibiting the secretion of microvesicles from cancer cells that are suitable for use in the methods described herein can be formulated, dosed, administered and delivered as described above for miR-21 inhibitor compounds.

The present invention is additionally based, in part, on the inventors' finding that microvesicles containing miR-21 fuse with myoblasts and promote apoptosis by activating Toll-like receptors (TLRs) on the myoblasts. Accordingly, in an additional embodiment, the present invention further relates to a method of treating cachexia in a patient who has a cancer, comprising administering to the patient an effective amount of at least one compound for inhibiting fusion of microvesicles from cancer cells with muscle cells or adipocytes in the patient. In a particular embodiment, the microvesicles contain a miR-21 gene product.

Compounds for inhibiting the fusion of microvesicles from cancer cells with muscle cells or adipocytes that are suitable for use in the methods described herein can be formulated, dosed, administered and delivered as described above for miR-21 inhibitor compounds.

A description of example embodiments of the invention follows.

Example: Microvesicles Containing miRNAs Promote Muscle Cell Death in Cancer Cachexia Via Toll-Like Receptor Signaling Introduction MicroRNAs (miRNAs) are a family of small, noncoding RNA molecules, 19-24 nucleotides in length, that are evolutionarily conserved and tissue-specific. These noncoding RNAs function by regulating gene expression through mRNA degradation or the inhibition of protein translation and are dysregulated in all cancers. Interestingly, miRNAs have also recently been discovered extracellularly, contained in body fluids such as serum, plasma, urine, milk, and spinal fluid. These circulating miRNAs are embedded in microvesicles (MVs)/exosomes, which are small, membrane-derived particles, usually 30 nm to 1 μm in size. Although the mechanism of extracellular formation and secretion is not well-defined, evidence indicates that such vesicles possess the capability to "communicate" with neighboring or distal cells by fusing with the plasma membrane and subsequently delivering their cargo, consisting of various molecules that include proteins, mRNAs, and miRNAs. Moreover, transported miRNAs are capable of targeting mRNAs in recipient cells.

MVs and exosomes are secreted from various cell types, and their miRNA content is associated with regulating cellular processes involved in cell communication, angiogenesis, and extracellular matrix remodeling.

Cachexia is a syndrome characterized by weight loss resulting from a reduction of lean body mass and fat mass that accompanies many types of chronic diseases, including cancer. The weight loss in cachexia is not caused by malnutrition or starvation but, rather, by inflammatory changes associated with the presence of the tumor and the production of cytokines. Patients with advanced lung cancer and pancreatic cancer, as well as other gastrointestinal malignancies, most often suffer from the cachexia syndrome that promotes asthenia, physical weakness, and mental fatigue. Patients with cachexia are more susceptible to dose-limiting chemotoxicity, and the degree of weight loss is positively correlated with mortality.

Cancer cachexia emaciates not only adipose tissue but also skeletal muscle, which together constitute 40% of total body weight in humans. Loss of skeletal muscle in cachexia originates from a decrease in protein synthesis as well as an increase in protein degradation resulting from an altered metabolism in response to a progressing tumor. Recently, it was reported that the deregulation of muscle stem cells is a contributing factor in the regulation of tumor-induced muscle wasting. In both tumor-bearing mice and patients with pancreatic cancer and weight loss, it was found that the transcription factor, Pax7, which controls the self-renewal of muscle stem cells, was persistently expressed. This sustained expression of Pax7 caused committed stem cells to be impaired in their differentiation program, resulting in their inability to fuse with damaged myofibers, which in turn enhanced muscle atrophy. These results showed that events in the muscle microenvironment are important in tumor-induced muscle wasting. In addition to events on muscle stem cells, apoptosis has also been associated with cancer cachexia and proposed to regulate skeletal muscle loss in various cachexia conditions, but exactly which populations of cells undergo cell death is not clear, nor is the mechanism causing cell death well-understood.

Materials and Methods

Cell Culture. All cell lines were purchased from American Type Culture Collection unless indicated otherwise. Human cancer cell lines A549, H460, AsPC-1, Panc-2, and MDA-MB-231 and murine Lewis Lung Carcinoma (LLC) cells were cultured in RPMI-1640 medium (Sigma-Aldrich) supplemented with 10% (vol/vol) FBS and maintained using standard conditions. C2C12, MCF7, mouse embryonic fibroblasts (MEFs), and MIA PaCa-2 were cultured in DMEM (Sigma-Aldrich) supplemented with 10% (vol/vol) FBS.

Microvesicle Isolation. For all experiments, microvesicles (MVs) were isolated from 250×106 cells cultured in serum-free medium for 48 h. Serum-free-conditioned media were then collected and harvested at 300×g for 10 min to eliminate large cells. The supernatant was then recovered, and successive centrifugations at increasing speed were performed: one at 2,000×g for 20 min to eliminate dead cells, then one at 10,000×g for 30 min to remove cell debris, and finally one ultracentrifuge at 100,000×g for 70 min to pellet MVs. The resulting pellet was then washed in PBS and ultracentrifuged again at the same speed. The obtained pellet was finally resuspended in 1 mL serum-free medium and used for treatment. MVs isolated from patient and mouse sera were isolated through ultracentrifugation as described earlier.

MV Treatment. C2C12 immortalized myoblasts or primary myoblasts isolated from mice were treated with MVs at indicated times. Cell numbers of myoblasts were counted on a hemocytometer.

Quantitative Real-Time PCR. Quantitative real-time PCR analysis for miRNAs was performed with the TaqMan MicroRNA assays kit (Applied Biosystems), according to the instructions of the manufacturer. Ath-miR159a and cel-miR-248 synthetic oligos were added to each sample to normalize the quantitative real-time PCR on RNAs extracted from MVs.

Nanosight. The MVs prepared from the above-mentioned cell lines were analyzed using a Nanosight NS300 (Nanosight Ltd). The MV preparations were stored at −80° C., thawed at room temperature, and diluted in PBS solution that was free of any contaminant particles. All samples were diluted to ~109 particles/mL for analysis. Video capture and analysis on the NS300 was used to create size and concentration profiles for each sample.

MTS Assay. The MTS assay kit was purchased from Promega (catalogue no. G3580), and cell viability was determined by using 96-well plate on a Spectra MAX M2 plate reader (Molecular Devices), following the manufacturer's protocol.

siRNA Transfection. For transfection of A549 cells with Exiqon Negative Control A or miRCURY, LNA inhibitor hsa-miR-21 Lipofectamine 2000 (Invitrogen) was used, following the manufacturer's instructions.

Single Fiber Isolation. Single myofibers were prepared from gastrocnemius muscles according to a previously established protocol (1). Isolated single myofibers were fixed with 2% formaldehyde and further analyzed with TUNEL (Roche, fluorescein) assay and immunofluorescence staining.

Myoblast Isolation and Culture. Primary myoblasts were isolated as previously described (2) and preplated twice, using noncoated tissue culture dishes, and then cultured either on a matrigelcoated 96-well plate for MTS assay reading at indicated times or on a matrigel-coated 12-well plate for protein and RNA analysis.

Immunofluorescence and TUNEL Staining. Immunofluorescence staining and Western blotting were performed as previously described (2). TUNEL staining was performed using an In Situ Cell Death Detection Kit (Roche), following the manufacturer's protocol. Quantitation was performed from 50 myofibers per muscle per animal.

Trypan Blue Staining. Trypan blue dye was purchased from Gibco (15250-061), and staining was performed following the manufacturer's protocol. Dead cells are blue in color under the microscope and were counted using a hemocytometer.

Western Blot. Western blots were performed as previously described (2). Antibodies used and their dilutions are listed: p-JNK (Cell Signaling Technology, 1:2,000), p-c-Jun (Cell Signaling Technology, 1:1,000), p-p38 (Cell Signaling Technology, 1:2,000), and vinculin (Abeam, 1:3,000).

Mice. Cachexia in the LLC model were induced as previously described (2). TLR7−/− mice were obtained from Jackson Laboratory. Wild-type C57B6 male mice at the same age and weight were used as TLR7+/+ controls. All genotypes were determined by PCR, using tail DNA. All procedures used in this study complied with federal guidelines and the institutional policies of the Ohio State University Animal Care and Use Committee.

Statistics. All quantitative data are represented as mean or mean±SEM. Analysis was performed between different groups, using a two-tailed Student t test. Statistical significance was set at a P value of 0.05 as significant and a value of 0.01 as highly significant.

Results and Discussion

Lung and Pancreatic Tumor-Derived MVs Induce Cell Death on Murine Myoblasts. Upon examining the role of muscle progenitors in cachexia, it was observed that a considerably higher number of apoptotic cells were associated with muscle cells from Lewis lung carcinoma (LLC) tumor-bearing mice, which suffered from severe cachexia, compared with those from tumor-free mice (FIGS. 5A and 5B). Interestingly, co-staining with TUNEL and the muscle stem cell marker, Pax7, revealed a significant increase of apoptotic muscle stem cells (FIGS. 1A and 1B). This increase in apoptotic stem cells correlated with an overall decrease in the number of muscle nuclei (FIG. 1C).

To determine the regulation of this apoptotic response, the effects of proinflammatory cytokines were tested. Incubation with individual cytokines or a mixture containing TNFα, IL-1β, IL-6, and IFN-γ had little or no effect on the viability of proliferating murine C2C12 myoblasts (FIG. 5C). Similar results were observed with primary myoblasts (FIG. 5D). However, use of conditioned media from cultured LLC cells promoted apoptosis of myoblasts within 24 h after the incubation compared with use of medium alone (FIGS. 1D and 1E). This suggested that factors secreted from tumor cells possessed a cell death activity on myoblasts. Because this activity did not seem to derive from inflammatory cytokines, the effects of LLC-prepared MVs were tested. Indeed, these MVs readily induced cell death when added to C2C12 myoblasts (FIGS. 1F and 1G). Importantly, this killing activity was reduced by 50.9% (P<0.01) when LLC-conditioned medium was depleted of MVs but was restored to 88.2% when MVs were reconstituted in conditioned medium that had been previously depleted of the same vesicles (FIG. 1H). This suggests that the cell killing effect derives specifically from MVs. MV-mediated cell death was not unique to mouse LLC cells, as a similar response was observed when Pax7+ muscle cells were exposed to either conditioned media or MVs isolated from a human lung cell line, A549, as well as three human pancreatic cancer cell lines: PC1, Panc-2, and MIA-PACA (FIGS. 1I and 1J, and FIGS. 5 F and 5G), which represents two cancer types that are commonly associated with cachexia. In contrast, cell death was not recapitulated with MVs derived from established human breast cancer cell lines (FIG. 5 E-G), which represents a cancer type that is less prone to inducing cachexia.

MVs Derived from Pancreatic Cancer Patient Sera Induce Cell Death. To substantiate these in vitro results, LLC cells were injected into wild-type mice to induce muscle wasting, and MVs were prepared from cachectic serum and subsequently incubated with proliferative myoblasts. Compared with serum from healthy mice, MVs from cachectic mice significantly enhanced the cell death of myoblasts (FIG. 2A). Importantly, a similar cell-killing activity was observed when MVs were prepared from serum from patients diagnosed with pancreatic adenocarcinoma (FIG. 2B). Taken together, these data strongly support that circulating MVs in the cachectic serum are responsible for inducing apoptosis of muscle progenitor cells.

MV-Induced Apoptosis of Murine Myoblasts Is Mediated by a TLR7 Receptor. To determine whether TLR signaling was involved in mediating MV-induced myoblast cell death primary myoblasts were isolated from TLR7+/+ or TLR7-/- mice and then incubated cells with LLC-conditioned medium. Compared with TLR7+/+ myoblasts, cell death was significantly reduced in TLR7-/- cells, suggesting that TLR7 is required for the killing effect. Significantly, depletion of MVs from LLC-conditioned media reduced cell death to control levels in both TLR7+/+ and TLR7-/- myoblasts, and cell death was restored to 92.1% when TLR7+/+, but not TLR7-/-, myoblasts were reconstituted with MVs from conditioned media originally depleted of MVs (FIGS. 3A and 3B). Furthermore, TLR7's involvement in myoblast cell death induced by MVs prepared from cachectic cancer patient sera was tested. Impressively, a similar protection from cell death was observed in primary TLR7-/- myoblasts exposed to MVs isolated from 5 of 7 pancreatic cancer patients (FIG. 3C), confirming the previous results.

Figure 4A:
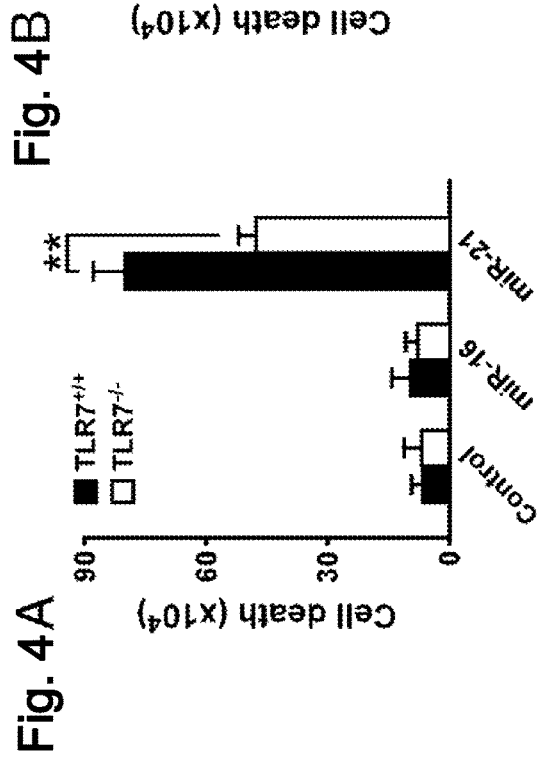
FIG. 4A is a graph depicting cell viability assessed with a cell counter for TLR7+/+ and TLR7−/− primary myoblasts that were treated with Dotap formulations of miR-16 and miR-21 for 24 h. As negative control, cells were incubated with Dotap alone. Experiments were performed in quadruplicate. Results are presented as average±SEM. $*P \leq 0.05$; $P \leq 0.01$; $*P \leq 0.001$.
Figure 6A:
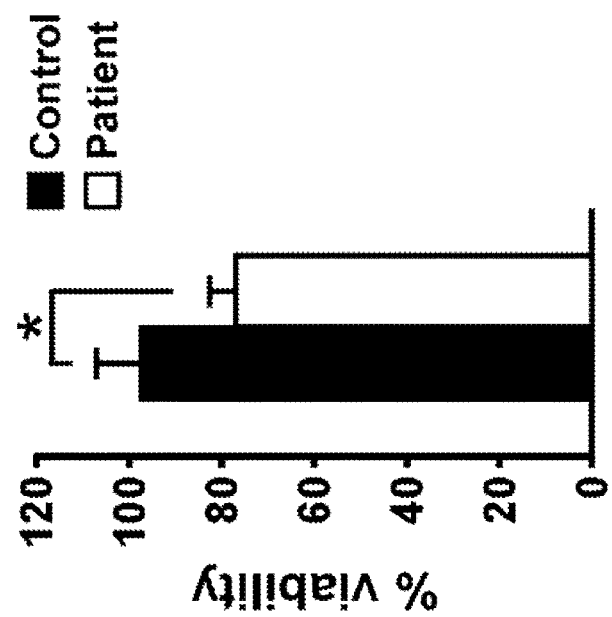
FIG. 6A is a graph depicting results of an MTS assay that was performed on C2C12 cells that had been incubated for 8 h with MVs isolated from the serum of control nontumor or LLC tumor-bearing mice. Experiment was performed in triplicate. Results are presented as average±SEM. $*P \leq 0.05$; $**P \leq 0.01$.
Figure 6B:
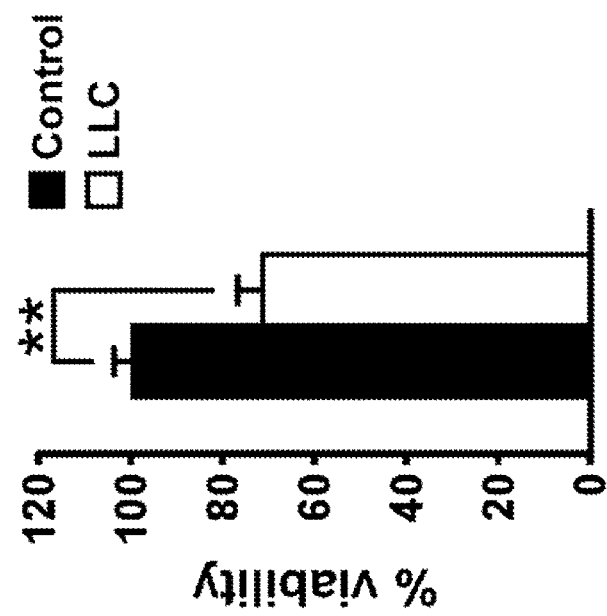
FIG. 6B is a graph depicting results of an MTS assay that was performed on primary myoblasts that had been incubated for 20 h with MVs isolated from the serum of patients who were diagnosed with pancreatic adenocarcinoma and who suffered from cancer cachexia. As control, MVs derived from the serum of healthy donors were used. Experiment was performed in triplicate. Results are presented as average±SEM. $*P \leq 0.05$; $**P \leq 0.01$.
Figure 7B:
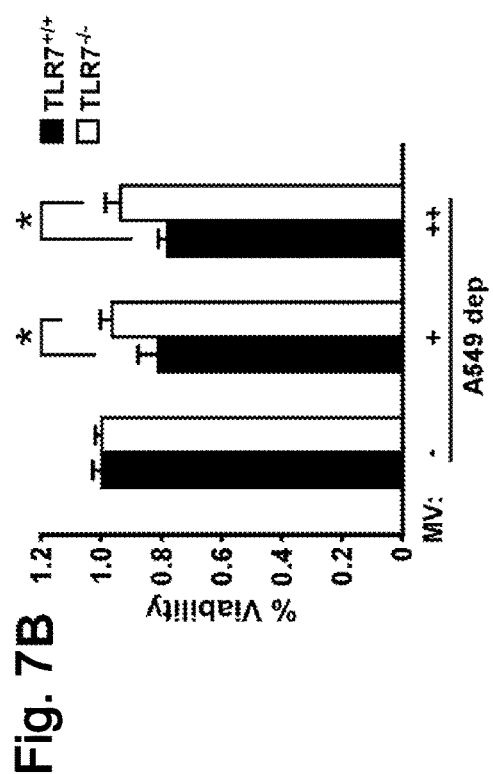
FIG. 7B is a graph depicting the results of an MTS assay for cell viability performed on primary myoblasts isolated from TLR7+/+ and TLR7−/− mice that had been incubated for 48 h with MVs derived from A549 cells diluted in medium depleted of MVs (A549 dep). "+" and "++" indicate a low and high amount of MVs being used for the treatment. Results are presented as average±SEM. $*P \leq 0.05$; $P \leq 0.01$; $*P \leq 0.001$.
Figure 7A:
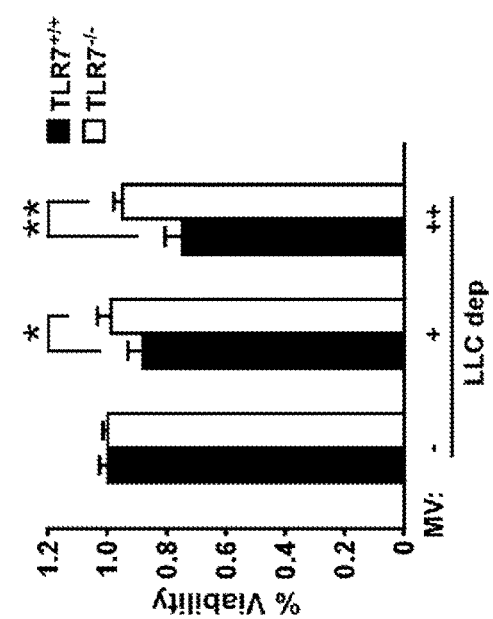
FIG. 7A is a graph depicting the results of an MTS assay for cell viability performed on primary myoblasts isolated from TLR7+/+ and TLR7−/− mice that had been incubated for 48 h with LLC-derived MVs diluted in LLC-conditioned medium depleted of MVs (LLC dep). "+" and "++" indicate a low and high amount of MVs being used for the treatment. Results are presented as average±SEM. $*P \leq 0.05$; $P \leq 0.01$; $*P \leq 0.001$.
Figure 7:
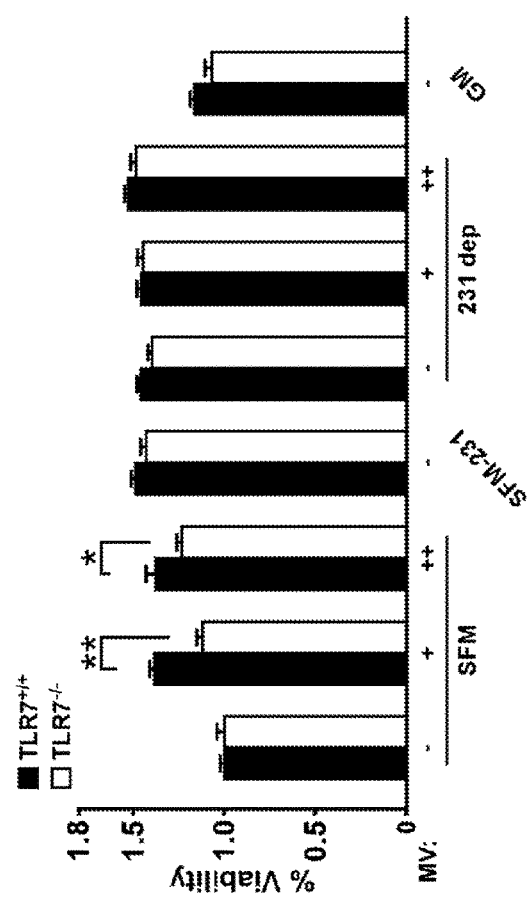
FIG. 7C is a graph depicting the results of an MTS assay for cell viability performed on primary myoblasts isolated from TLR7+/+ and TLR7−/− mice that had been incubated for 8 h with MDA-MB-231-derived MVs diluted in either serum-free medium (SFM) or MDAMB-231-conditioned SFM depleted of MVs (231 dep). Conditioned medium derived from MDA-MB-231 cells (SFM-231) or growth medium (GM) were used to treat primary myoblasts as controls. Results are presented as average±SEM. *P≤0.05; P≤0.01; *P≤0.001.
FIG. 7D is a graph depicting the results of an MTS assay for cell viability performed on primary myoblasts from TLR7+/+ and TLR7−/− mice that had been treated for 20 hours with MVs isolated from control sera of healthy donors (n=2) or cachectic sera (n=7) of pancreatic cancer patients who suffered from cachexia (Patient serum). Results are presented as average±SEM. *P≤0.05; P≤0.01; *P≤0.001.
Figure 7:
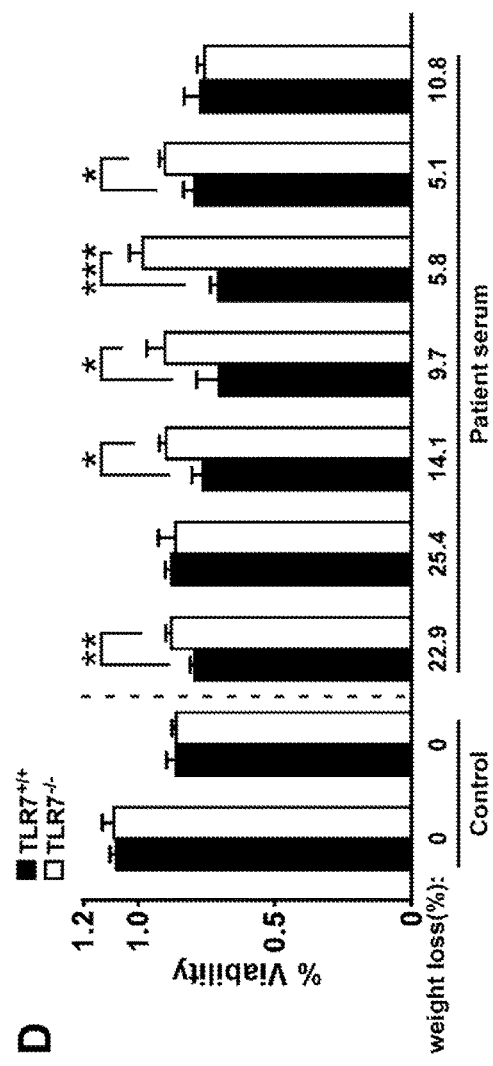
Figure 8:
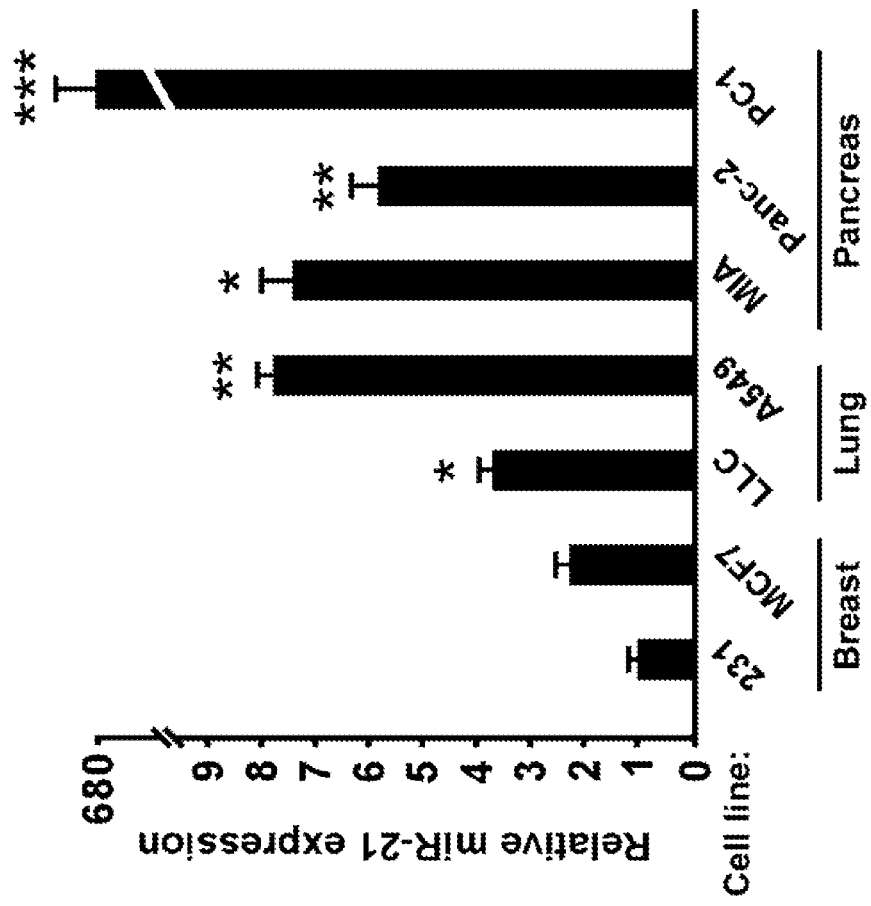
FIG. 8A is a graph depicting the results of quantitative real-time PCR performed on the MVs isolated from indicated cancer cell lines. Data were normalized with respect to exogenous controls ath-miR159a and cel-miR-248. Nanosight analysis was performed to determine the amount of MVs secreted per cell, and the expression level of miR-21 in MVs was further normalized to the MV number secreted per cell. Graph represents the relative expression level of miR-21 in the total MVs secreted per cell, with the lowest number set as 1 from the 231 cell line. Treatments with MVs derived from MDA-MB-231, MIA-PaCa-2, and AsPC-1 are indicated as 231, MIA, and PC1, respectively.
FIG. 8B is a graph depicting the results of an MTS assay that was performed on TLR7+/+ and TLR7−/− primary myoblasts that had been incubated for 48 h with Dotap formulation of miR-16, miR-21, or Dotap alone. Results are presented as average±SEM. *P≤0.05; **P≤0.01.
FIG. 8C is a graph depicting the results of an MTS assay that was performed on TLR7+/+ and TLR7−/− C2C12 cells that had been incubated for 48 h with Dotap formulation of miR-16, miR-21, or Dotap alone. Results are presented as average±SEM. *P≤0.05; **P≤0.01.
FIG. 8D is a graph depicting the results of an MTS assay that was performed on TLR7+/+ and TLR7−/− primary myoblasts that had been incubated with MVs derived from A549 cells previously transfected with LNA-anti-miR-21. Results are presented as average±SEM. *P≤0.05; **P≤0.01.
Figure 9:
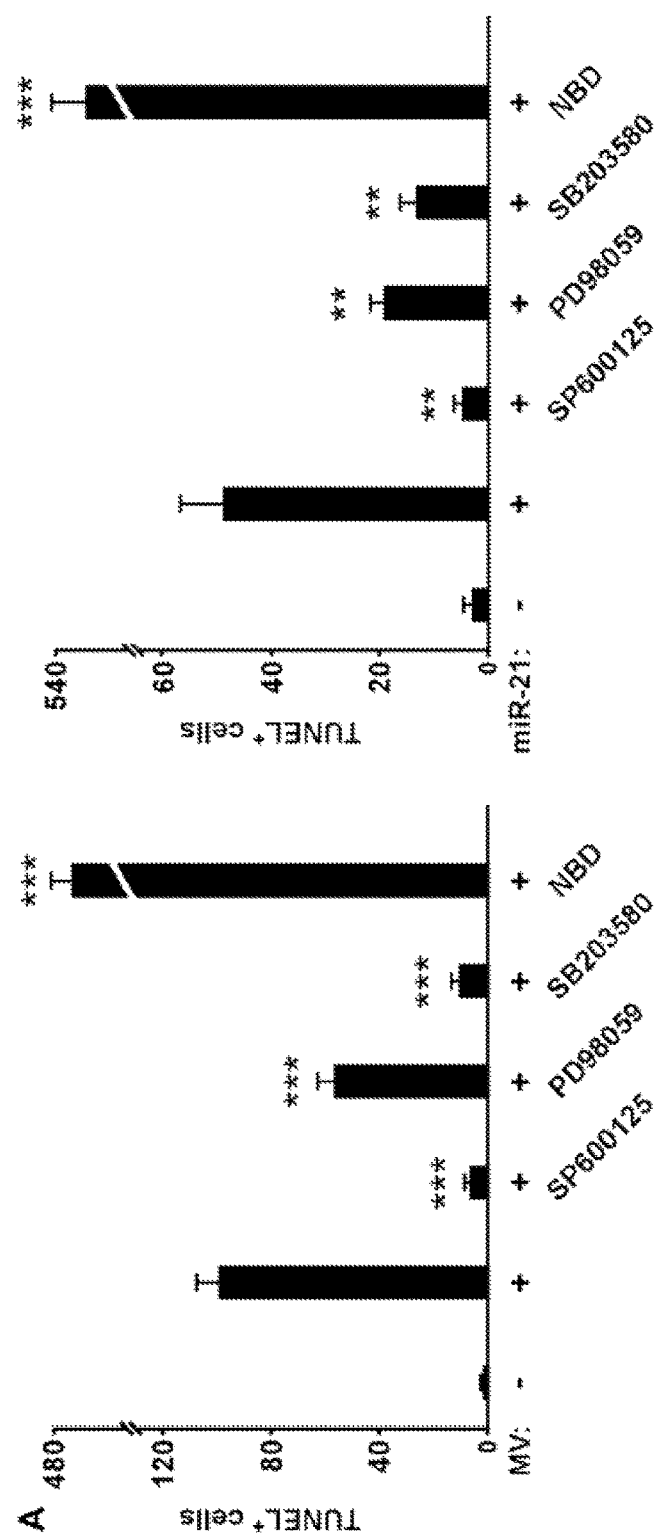
FIG. 9A is a graph depicting apoptosis, as assessed by TUNEL staining, of C2C12 cells that had been pretreated for 1 h with either DMSO (control) or different apoptosis inhibitors (SP600125, phosphor-c-jun inhibitor; PD98059, MEK inhibitor; SB203580, p38 inhibitor) or NF-κB inhibitor (NBD) before being treated for 8 h with MVs isolated from A549 cells (Left graph) or synthetic miR-21 (Right graph). "+" indicates MVs or synthetic miR-21 being added. Results are presented as average±SEM. P≤0.01; *P≤0.001.
FIG. 9B is an image of a Western blot on extracts of C2C12 cells that had been treated with either LLC-derived MVs (Upper) or synthetic miR-21 (Lower, using miR-16 as control), which were probed with antibodies against phospho-JNK, phospho-c-jun, and phospho-p38 at different times, as indicated.
Figure 9:
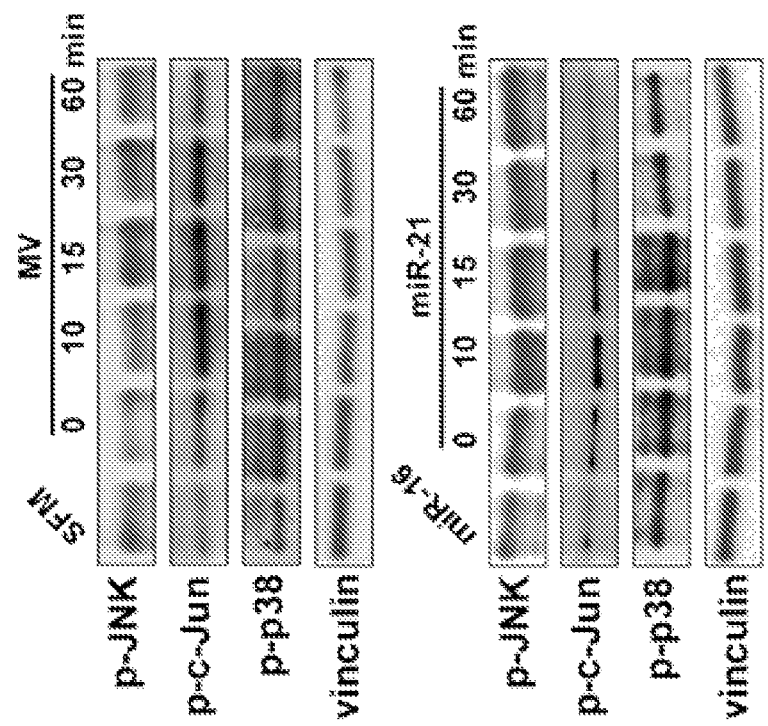

MV Cargo miR-21 Promotes Apoptosis Through JNK Activation. To test whether miR-21 contributed to TLR7-mediated cell death of progenitor myoblasts, miR-21 expression levels within MVs derived from cancer cell lines were evaluated. Results showed that miR-21 expression was elevated in MVs secreted by lung and pancreatic cancer cell lines that induced myoblast cell death compared with MVs from breast cancer cell lines that have little effect on the muscle cell viability (FIG. 8A). Moreover, the exogenous addition of miR-21 induced pronounced cell death in TLR7+/+ primary myoblasts, but this response was significantly blunted in TLR7-/- cells (FIG. 4A). In comparison controls, Dotap treatment alone or overexpression of miR-16 did not recapitulate this same cell death response. Finally, MVs prepared from LLC cells that had been depleted of miR-21 strongly reduced MV-mediated killing of C2C12 myoblasts, as well as primary TLR7+/+ myoblasts (FIG. 4B). To investigate what signaling pathways MVs and miR-21 activated to mediate cell killing of myoblasts, cells were treated with MVs or miR-21 in the absence or presence of pharmacological inhibitors for JNK, ERK1/2, p38α/β, and NF-κB, which have all been implicated in regulating apoptosis. Inhibitors of JNK and p38 were effective at significantly reducing myoblast apoptosis in the presence of MVs or miR-21; interestingly, inhibition of NF-κB accentuated cell killing (FIG. 9A). To substantiate the relevance of JNK and p38, the activation of these pathways was tested in the presence of MVs and miR-21. Results showed that JNK and c-JUN were transiently induced in proliferating myoblasts under MVs and miR-21 exposure, whereas no significant change was seen with p38 activity (FIG. 9B). These data support that MVs containing miR-21 signal through TLR7 downstream to JNK to promote cell death of muscle myoblasts. The increase in cell death observed by inhibition of NF-κB is consistent with the notion from previous findings that this occurs through activation of JNK.

The results described herein indicate that circulating MVs secreted by mouse and human cancer cells cause apoptosis of muscle cells, and that this phenomenon is dependent on TLR7 (mouse) or TLR8 (human). Importantly, cancer cell lines that are usually associated with cancer cachexia, such as lung cancer and pancreatic cancer cell lines, were able to induce myoblast cell death, but not in breast cancer cell lines, which are not as strongly associated with cachexia. These results suggest the specificity of MV-mediated cell death in the context of muscle wasting associated with cancer cachexia.

It was further found that miR-21 levels secreted into the MVs were elevated in those cell lines that induced muscle cell death. One of the pancreatic cell lines, PC1, induced the strongest effect of cell death (FIGS. 5F and 5G) and contained the highest levels of miR-21 in the MV cargo. Inhibition of miR-21, a ligand of TLR7 and TLR8, inhibited the induction of apoptosis of the muscle cells. Thus, on the basis of these findings, it was predicted that MVs secreted by cancer cells overexpressing miR-21 fuse with muscle cells and induce apoptosis by activating TLR7/8.

One interesting observation is that cancer cell lines that induce muscle cell death also seem to secrete more MVs (Table 1), which contributes to the phenomenon of a higher level of miR21 expression. However, blocking TLR7 does not completely rescue miR21-induced cell death (FIG. 8A).

TABLE 1

| Quantitation of secreted MV number | |
|---|---|
| Cancer cell lines | MV number per cell |
| AsPC-1 | $9.8 \times 10^7$ |
| MIA-PaCa | $1.6 \times 10^7$ |
| LLC | $1.46 \times 10^7$ |
| Panc-2 | $5 \times 10^6$ |
| A549 | $2.8 \times 10^6$ |
| MEFs | $1.3 \times 10^6$ |
| MDA-MB-231 | $9.6 \times 10^5$ |
| MCF7 | $7.44 \times 10^5$ |

Cancer cell lines secrete different amount of MVs. MVs isolated from cancer cell lines were subjected to Nanosight analysis. Values reflect average number of MVs secreted per cell for each indicated cell line.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating cachexia in a cancer patient in need thereof, comprising administering to the patient an effective amount of at least one compound for inhibiting the expression or activity of a miR-21 gene product.

2. The method of claim 1, wherein the miR-21 gene product is a mature miR-21 RNA.

3. The method of claim 1, wherein the miR-21 gene product is a pre-cursor miR-21 RNA.

4. The method of claim 1 wherein the compound inhibits binding of the miR-21 gene product to a Toll-like receptor 7 (TLR7 receptor) or a Toll-like receptor 8 (TLR8 receptor).

5. The method of claim 1, wherein the compound is an antisense nucleic acid that binds to a miR-21 gene product.

6. The method of claim 1, wherein the compound is a double-stranded RNA molecule having at least 90% sequence homology with a miR-21 gene product.

7. The method of claim 1, wherein the compound is a ribozyme.

8. The method of claim 1, wherein the cancer is lung cancer.

9. The method of claim 1, wherein the cancer is pancreatic cancer.

10. The method of claim 1, wherein the cancer is gastric cancer.

11. The method of claim 1, wherein the cancer is esophageal cancer.

12. The method of claim 1, wherein the cancer is duodenal cancer.

13. The method of claim 1, wherein a nucleic acid that expresses the compound for inhibiting the expression of a gene encoding a miR-21 gene product is administered to the cancer patient.

14. The method of claim 1, wherein the cancer patient is a human.

15. The method of claim 1, further comprising administering to the cancer patient an effective amount of at least one compound for inhibiting the expression or activity of a microRNA that is present in microvesicles secreted from cancer cells in the patient, wherein the microRNA is miR-27b, miR-29a, miR-92a, miR-126, miR-133, miR-146, miR-147, miR-155 or miR-574-5p, or a combination thereof.

* * * * *